US012636108B2

(12) United States Patent
Takahashi et al.

(10) Patent No.: US 12,636,108 B2
(45) Date of Patent: May 26, 2026

(54) ROBOTIC SURGICAL SYSTEM AND METHOD OF CONTROLLING ROBOTIC SURGICAL SYSTEM

(71) Applicant: KAWASAKI JUKOGYO KABUSHIKI KAISHA, Kobe (JP)

(72) Inventors: Kaoru Takahashi, Kobe (JP); Ayataka Kobayashi, Kobe (JP); Hidenori Tani, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 56 days.

(21) Appl. No.: 18/783,977

(22) Filed: Jul. 25, 2024

(65) Prior Publication Data

US 2024/0374332 A1 Nov. 14, 2024

Related U.S. Application Data

(63) Continuation of application No. PCT/JP2023/004320, filed on Feb. 9, 2023.

(30) Foreign Application Priority Data

Feb. 28, 2022 (JP) ................................. 2022-030319

(51) Int. Cl.
*B25J 15/02* (2006.01)
*A61B 34/00* (2016.01)
(Continued)

(52) U.S. Cl.
CPC .............. *A61B 34/71* (2016.02); *A61B 34/37* (2016.02); *A61B 2090/067* (2016.02)

(58) Field of Classification Search
CPC ........ A61B 2090/066; A61B 2090/067; A61B 34/30; A61B 34/35; A61B 34/37; A61B 34/71; B25J 15/02; B25J 15/08
(Continued)

(56) References Cited

U.S. PATENT DOCUMENTS

| 8,147,414 B2 * | 4/2012 | Abraham | ............... A61B 8/445 |
| | | | 600/459 |
| 9,014,856 B2 * | 4/2015 | Manzo | ................... A61B 34/37 |
| | | | 901/19 |

(Continued)

FOREIGN PATENT DOCUMENTS

| JP | 2010-082309 A | 4/2010 |
| JP | 2022-181066 A | 12/2022 |

*Primary Examiner* — Jonathan L Sample
(74) *Attorney, Agent, or Firm* — METROLEX IP LAW GROUP, PLLC; Robert L. Scott, Esq.

(57) ABSTRACT

A robotic surgical system according to an embodiment may include: a surgical instrument including a pair of jaw members configured to be opened and closed by an elongate element; a robotic arm which includes a motor configured to drive the elongate element and to which the surgical instrument is attached; a first storage that stores in advance a first value corresponding to a rotation angle of the motor for a predetermined current value; and a controller configured to acquire a second value corresponding to the rotation angle of the motor when the predetermined current value is reached, and perform calibration to change, based on the acquired second value and the first value stored in the first storage, a command angle for a tightening operation of the jaw members.

20 Claims, 10 Drawing Sheets

(51) Int. Cl.
  *A61B 34/37*   (2016.01)
  *A61B 90/00*   (2016.01)

(58) Field of Classification Search
  USPC ................................................. 700/245–264
  See application file for complete search history.

(56)      References Cited

U.S. PATENT DOCUMENTS

| | | | | |
|---|---|---|---|---|
| 9,173,713 | B2 * | 11/2015 | Hart ........................ | A61B 34/71 |
| 11,406,457 | B2 * | 8/2022 | Yu .......................... | A61B 90/96 |
| 2008/0046122 | A1 * | 2/2008 | Manzo ................... | A61B 90/98 |
| | | | | 700/245 |
| 2010/0079099 | A1 * | 4/2010 | Katsuki ................. | A61B 34/71 |
| | | | | 318/565 |
| 2014/0200596 | A1 * | 7/2014 | Weir ....................... | A61B 34/30 |
| | | | | 227/176.1 |
| 2014/0200612 | A1 * | 7/2014 | Weir ...................... | A61B 90/98 |
| | | | | 227/176.1 |
| 2014/0200851 | A1 * | 7/2014 | Weir ................. | H02K 11/0094 |
| | | | | 702/182 |
| 2018/0049818 | A1 * | 2/2018 | Yates ..................... | A61B 34/37 |
| 2018/0161052 | A1 * | 6/2018 | Weir ................. | A61B 18/1445 |
| 2018/0353252 | A1 * | 12/2018 | Chassot ................. | A61B 17/00 |
| 2019/0274769 | A1 * | 9/2019 | Perdue ................... | A61B 34/35 |
| 2021/0045826 | A1 | 2/2021 | Asadian et al. | |
| 2021/0282876 | A1 * | 9/2021 | Ergueta Tejerina ... | A61B 17/28 |
| 2022/0047347 | A1 * | 2/2022 | Maughan .............. | G16H 40/63 |
| 2022/0378455 | A1 * | 12/2022 | Takahashi ............. | A61B 34/71 |
| 2023/0046044 | A1 * | 2/2023 | Zhang ................... | A61B 34/71 |
| 2023/0112334 | A1 * | 4/2023 | Zhang ................... | A61B 34/71 |
| | | | | 606/1 |

\* cited by examiner

[FIG. 1]
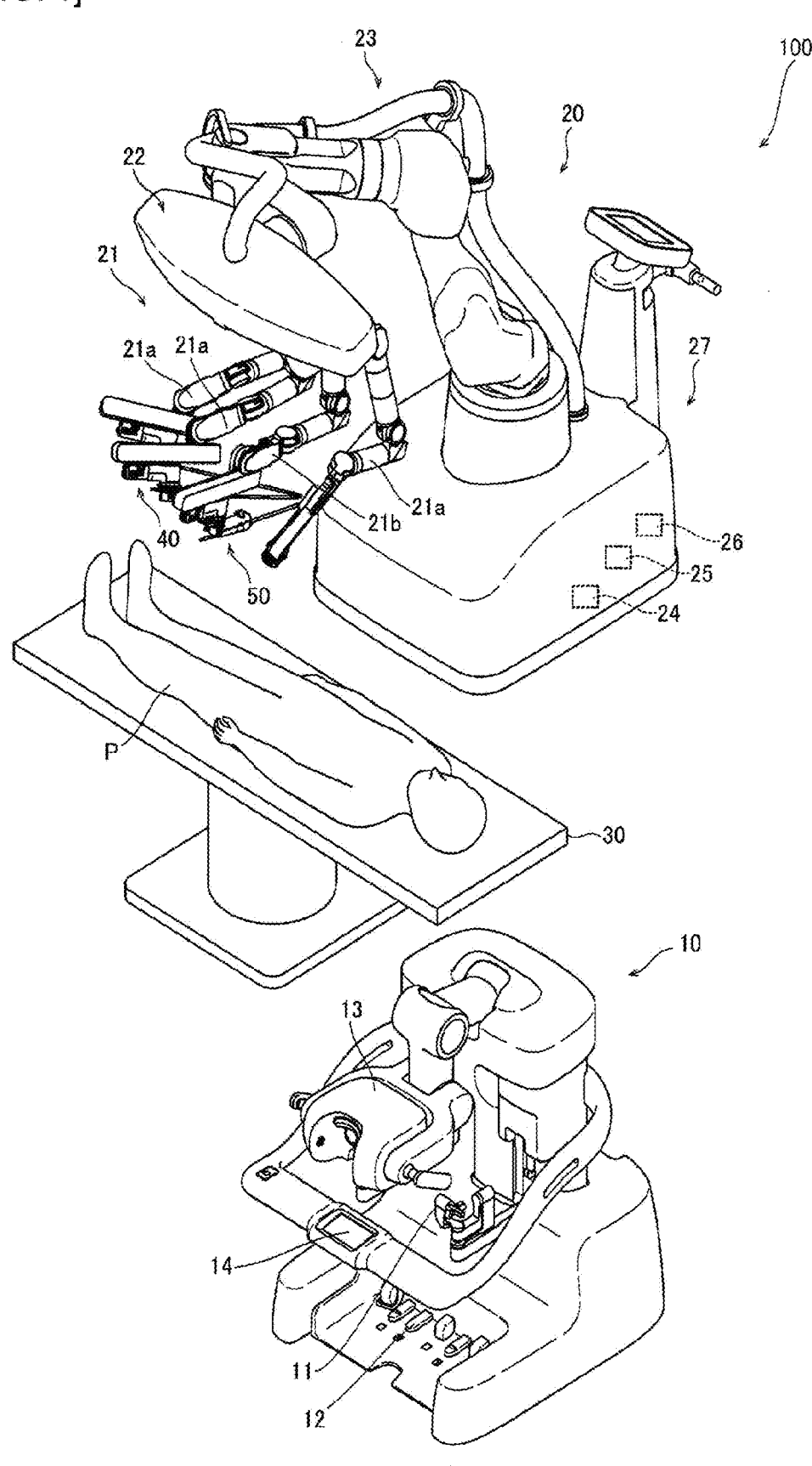

[FIG. 2]
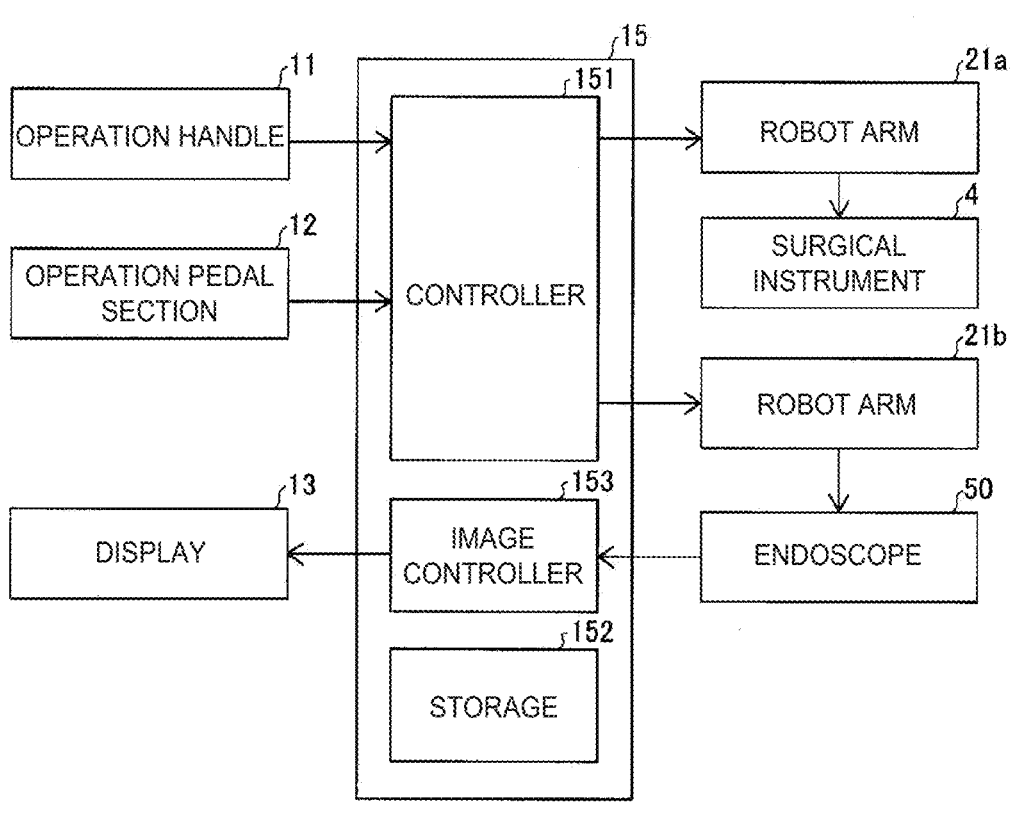
[FIG. 3]

[FIG. 4]
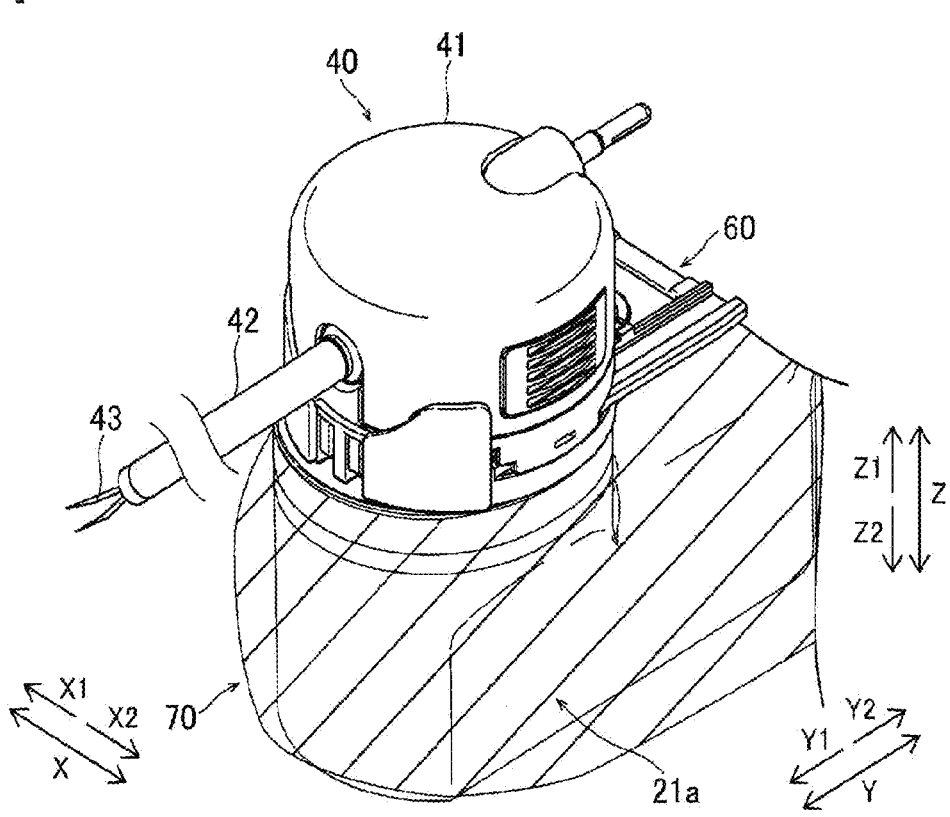

[FIG. 5]
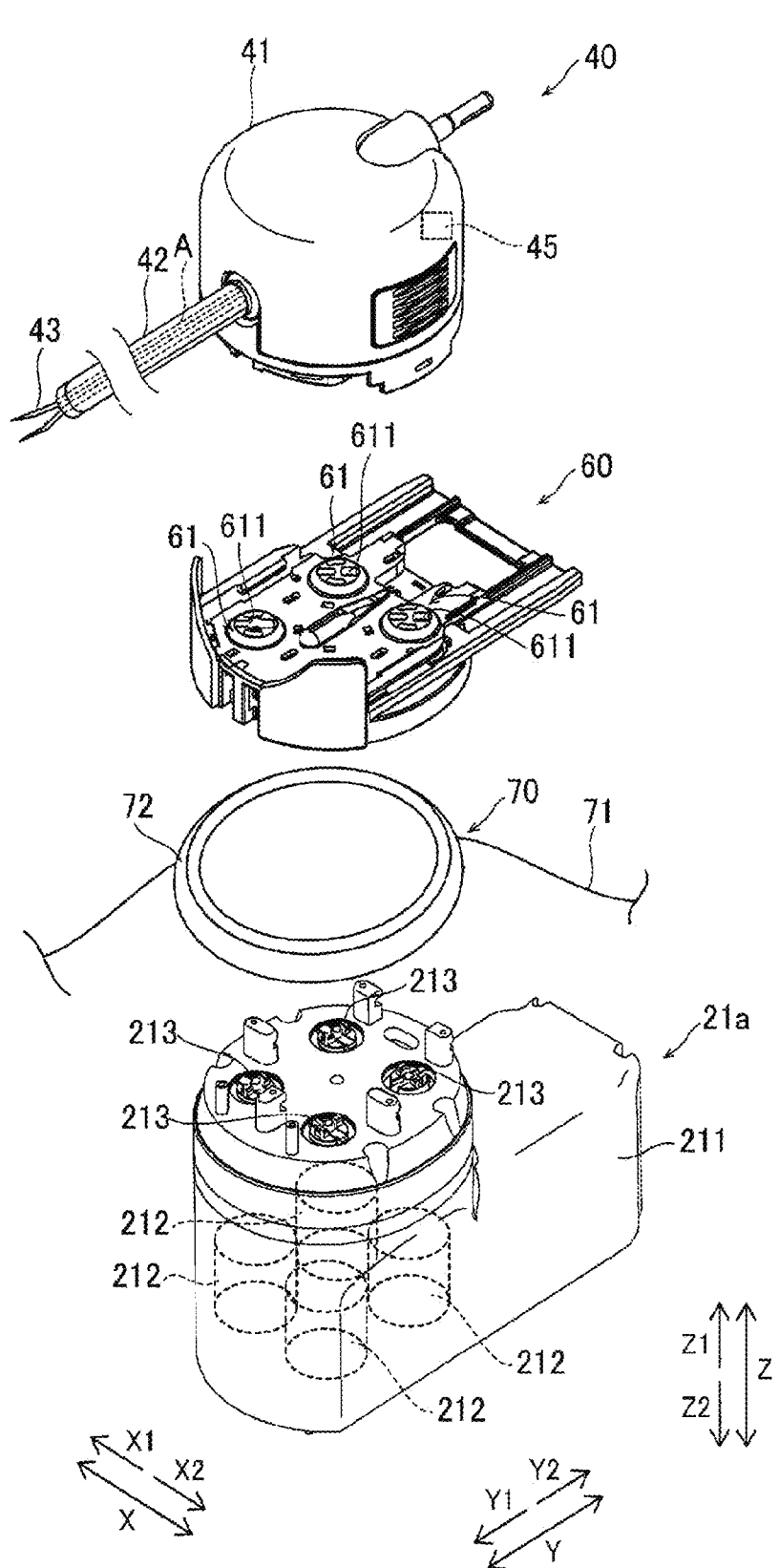

[FIG. 6]
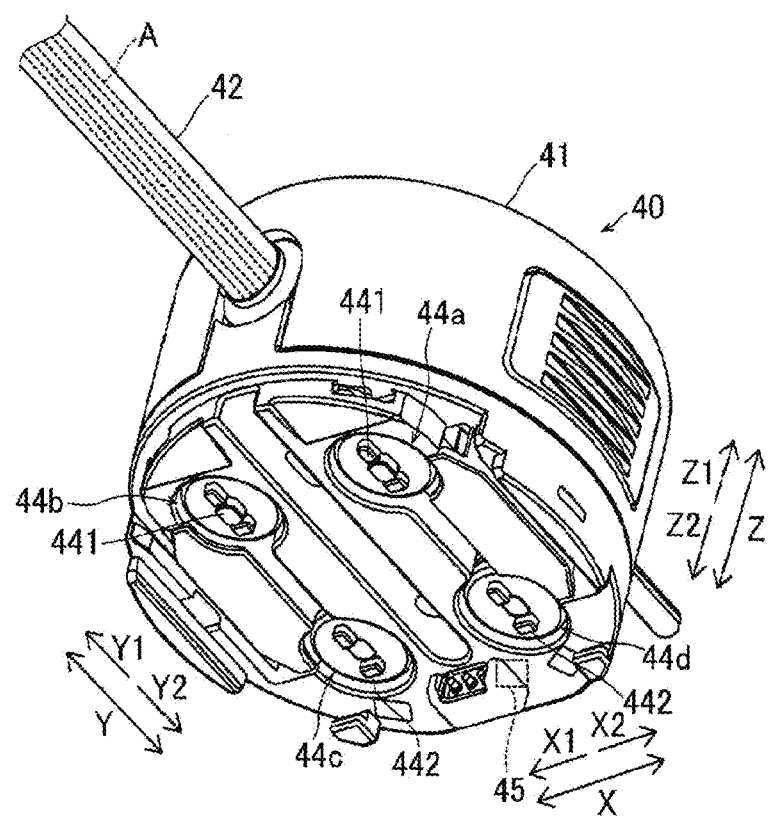
[FIG. 7]
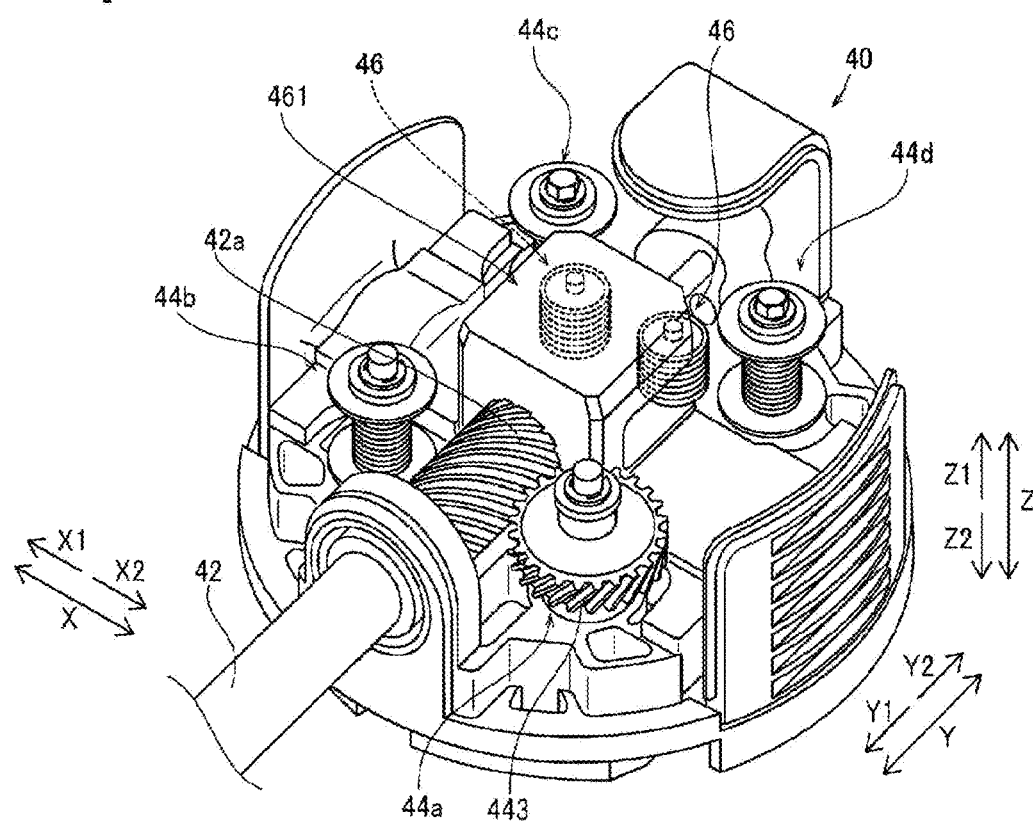

[FIG. 8]
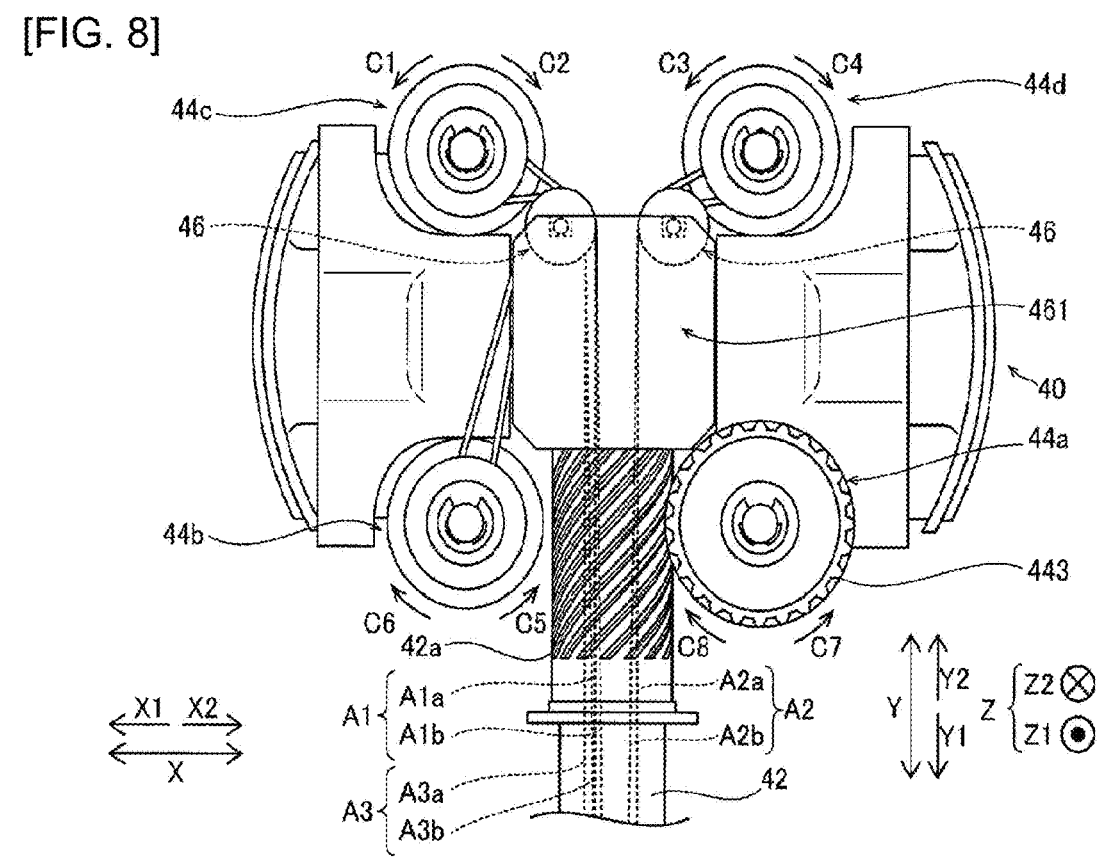
[FIG. 9]
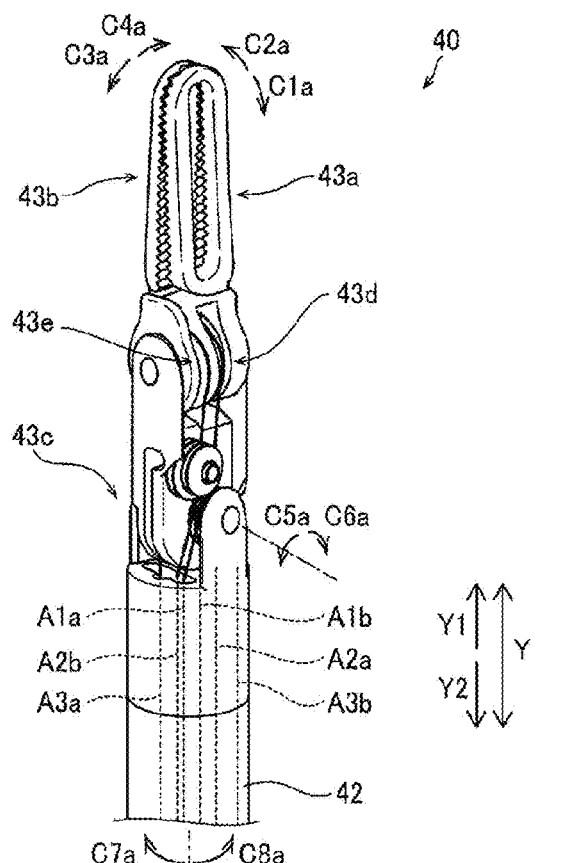

[FIG. 10]
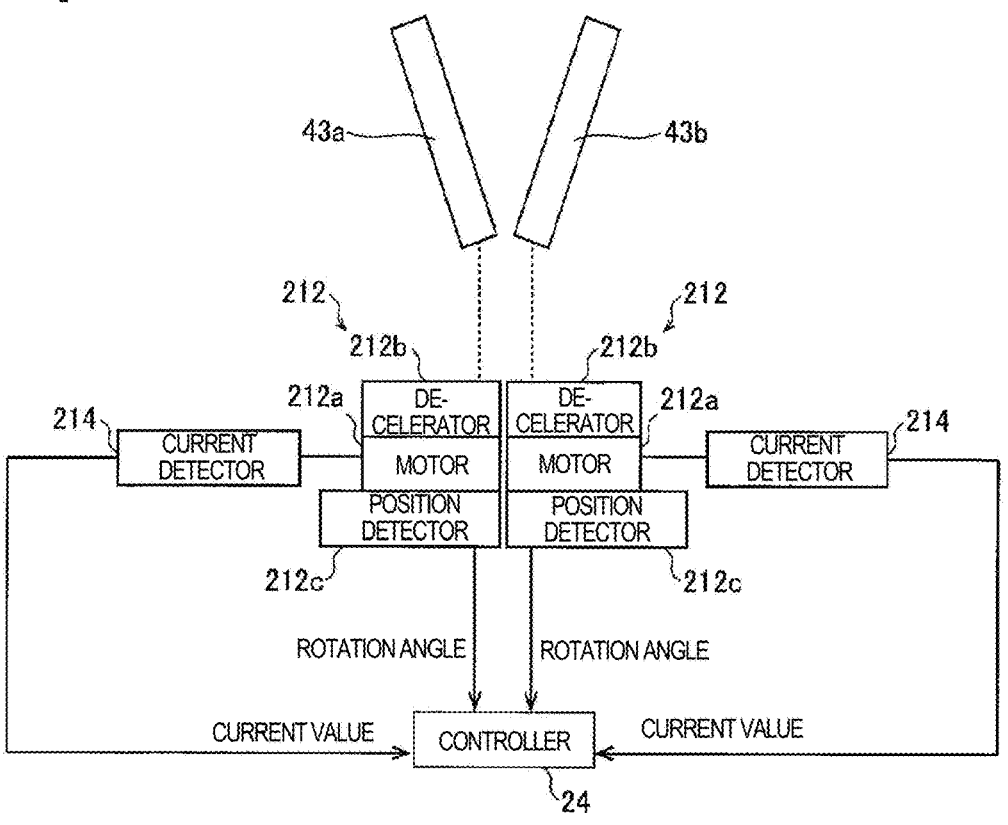
[FIG. 11]
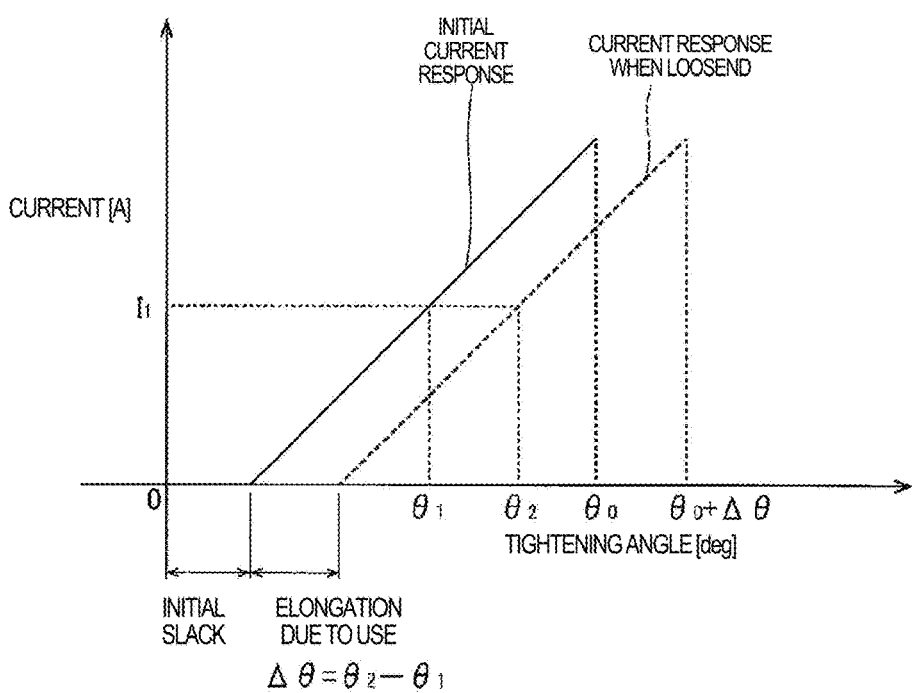

[FIG. 12]
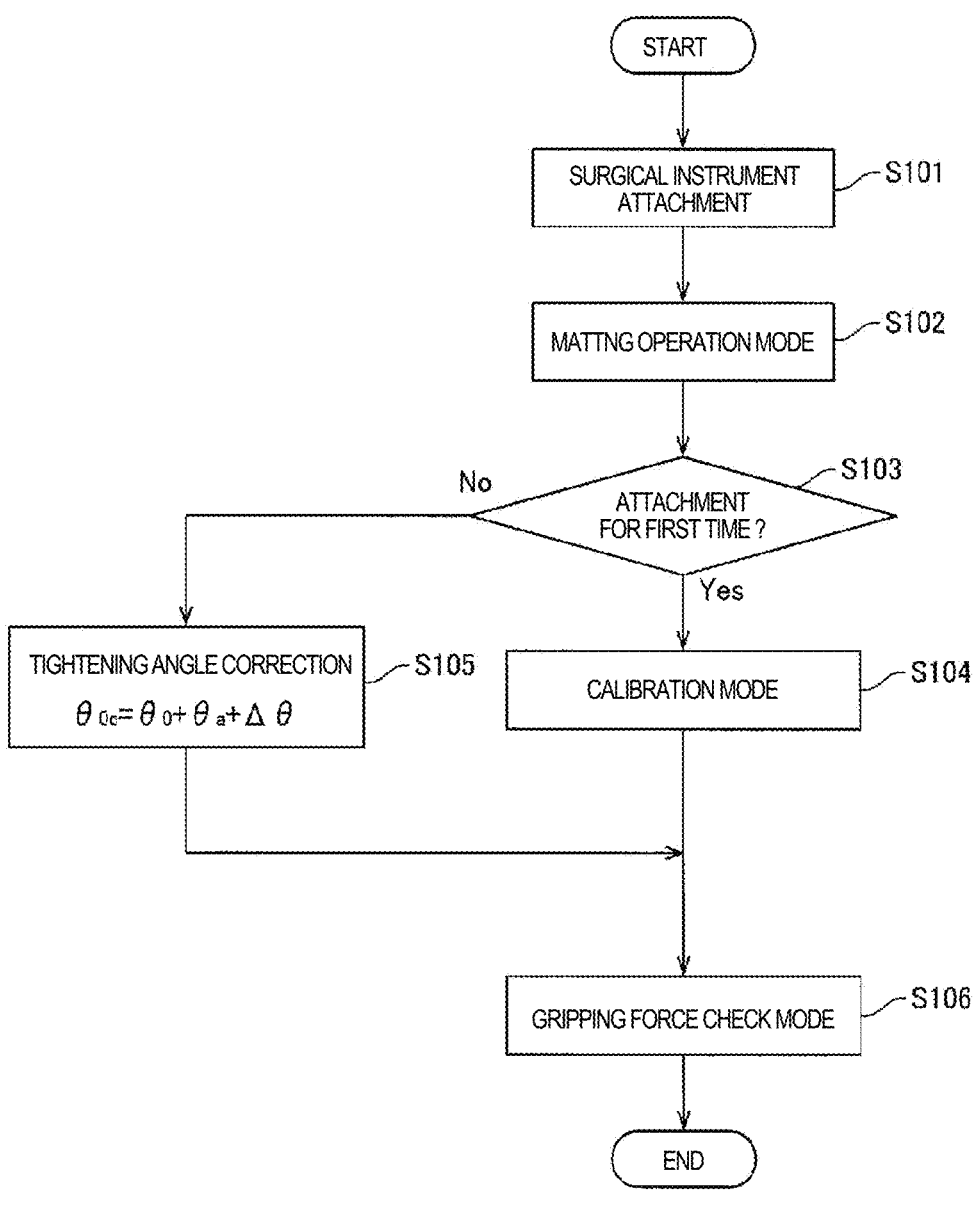

[FIG. 13]
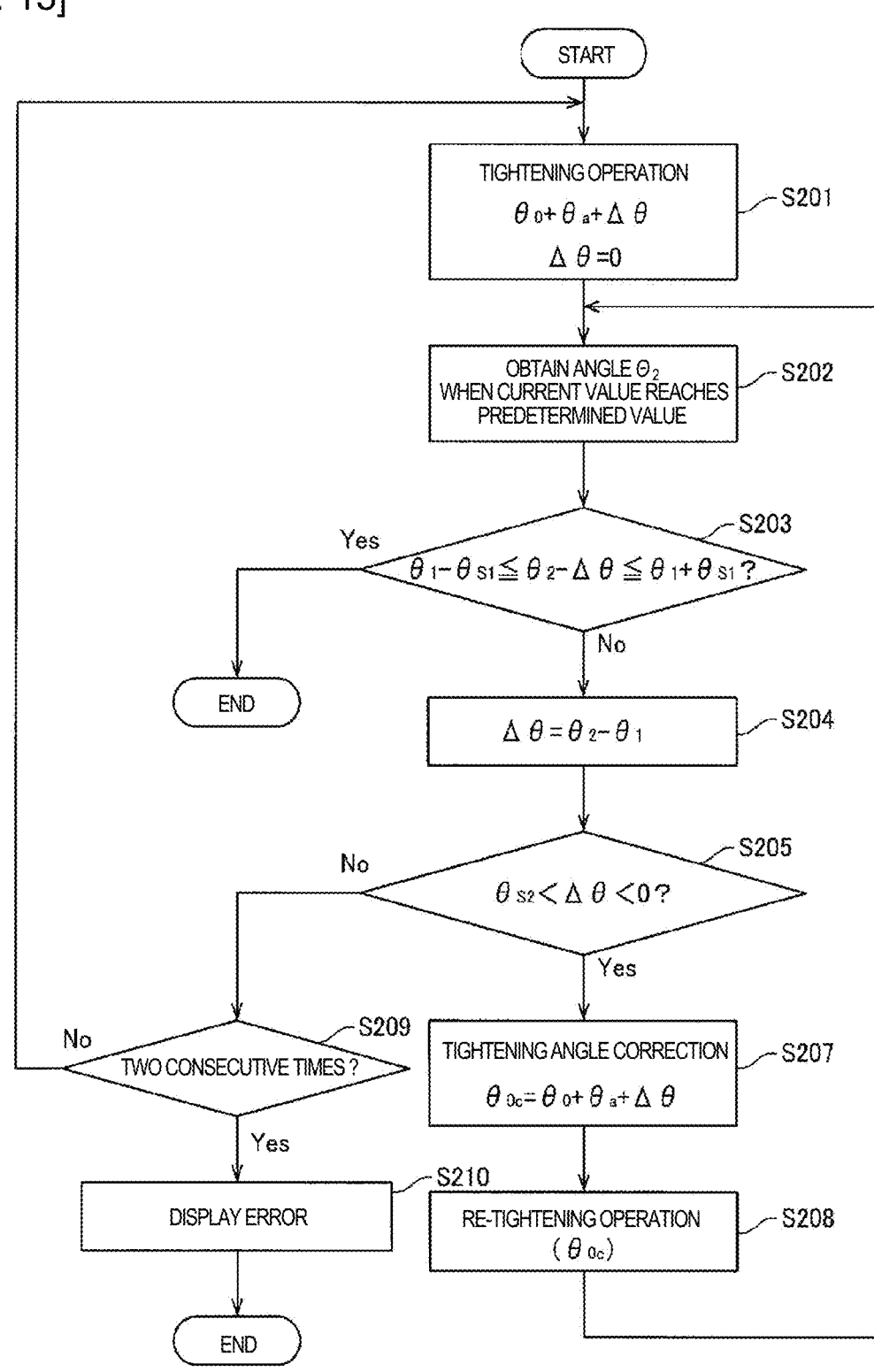

[FIG. 14]
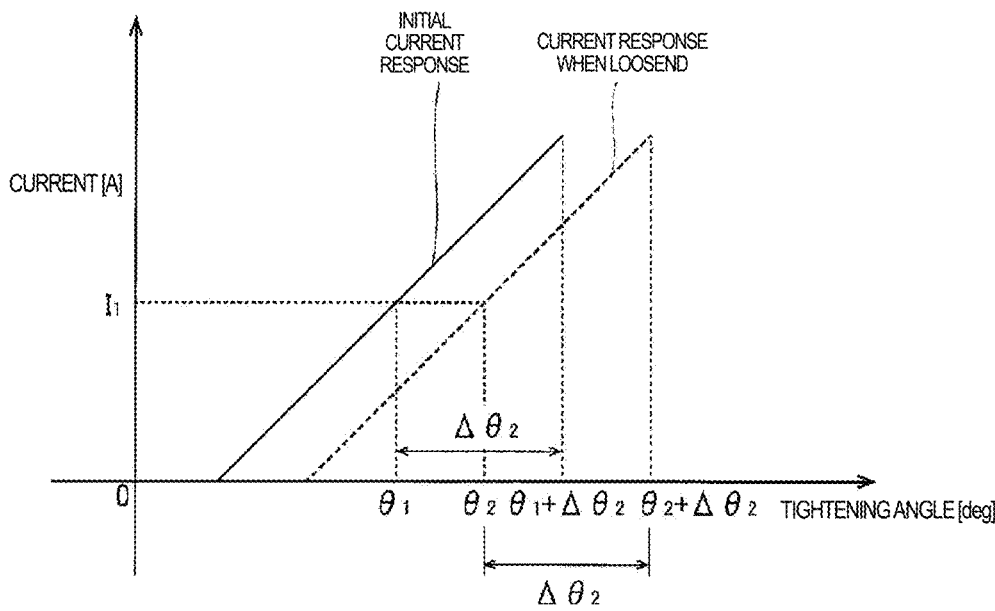
[FIG. 15]
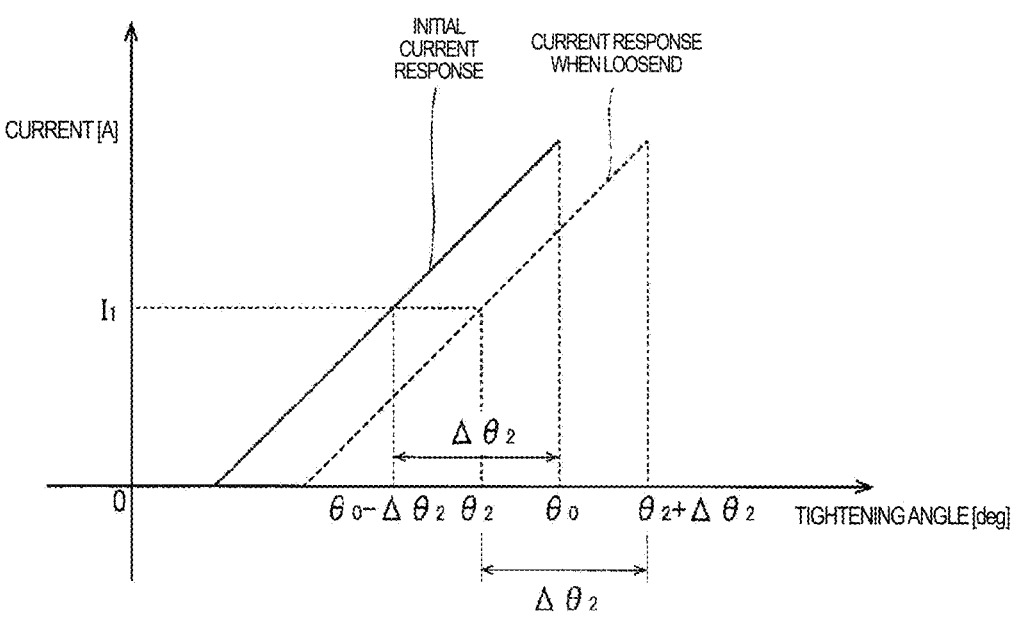

ROBOTIC SURGICAL SYSTEM AND METHOD OF CONTROLLING ROBOTIC SURGICAL SYSTEM

CROSS REFERENCE TO RELATED APPLICATIONS

This application is a continuation of International Application No. PCT/JP2023/004320, which is based upon and claims the benefit of priority from the prior Japanese Patent Application No. 2022-030319, filed on Feb. 28, 2022, the entire contents of all of which are incorporated herein by reference.

BACKGROUND

The disclosure may relate to a robotic surgical system and a method of controlling a robotic surgical system, and more particularly to a robotic surgical system and a method of controlling a robotic surgical system in which a drive of a pair of jaw members is controlled based on a rotation angle of a motor.

In a related art, a robotic surgical system is known that includes a surgical instrument including a pair of jaw members that are opened and closed by cables. Such a robotic surgical system is disclosed in U.S. Pat. No. 9,014,856, for example.

The above-mentioned U.S. Pat. No. 9,014,856 discloses a robotic surgical system including a surgical instrument including a pair of jaw members that are opened and closed by cables. In this robotic surgical system, as the surgical instrument is used over time, the cables that drive the pair of jaw members stretch, which may cause the pair of jaw members to be unable to exert a desired gripping force. Accordingly, the system compensates for such cable stretch. Specifically, in this robotic surgical system, a motor is torque-controlled so as to drive the jaw members within a predetermined torque range between an upper limit torque and a lower limit torque.

PATENT DOCUMENT 1: U.S. Pat. No. 9,014,856

SUMMARY

In the robotic surgical system described in the above listed U.S. Pat. No. 9,014,856, the motor that drives the jaw members is controlled based on the torque; however, in some cases, it is effective to use the rotation angle to control the motor that drives the jaw members. For example, in a case in which a motor is torque-controlled, if a decelerator with a high reduction ratio is used, a behavior of a distal end side of the surgical instrument is less likely to be reflected as a change in the motor torque. In this case, it becomes difficult to detect the behavior of the distal end side of the surgical instrument by detecting changes in the torque of the motor. In order to solve this problem, it is effective to control the motor that drives the jaw members based on the rotation angle thereof. However, in a case in which the motor that drives the jaw members is controlled based on the rotation angle thereof, the method described in the above-mentioned U.S. Pat. No. 9,014,856 cannot be used. For this reason, it is desirable to suppress a decrease in the gripping force of the jaw members in a configuration in which the drive of the jaw members is controlled based on the rotation angle of the motor.

An embodiment of disclosure may provide a robotic surgical system and a method of controlling a robotic surgical system that are capable of suppressing a decrease in a gripping force of jaw members in a configuration in which a drive of the jaw members of a surgical instrument is controlled based on a rotation angle of a motor.

A robotic surgical system according to a first aspect may include a surgical instrument including a pair of jaw members configured to be opened and closed by an elongate element; a robotic arm which includes a motor configured to drive the elongate element and to which the surgical instrument is attached; a first storage that stores in advance a first value corresponding to a rotation angle of the motor when a predetermined current value is reached; and a controller that is configured to acquire a second value corresponding to the rotation angle of the motor when the predetermined current value is reached, and perform calibration to change, based on the acquired second value and the first value stored in the first storage, a command angle for a tightening operation of the jaw members.

According to the first aspect, the controller is provided that acquires the second value corresponding to the rotation angle of the motor when the predetermined current value is reached, and performs the calibration to change the command angle for the tightening operation of the jaw members based on the acquired second value and the first value stored in the first storage. Accordingly, in a configuration in which the drive of the jaw members of the surgical instrument is controlled according to the rotation angle of the motor, it is possible to perform the calibration to compensate for the stretch of the elongate element. Therefore, in the configuration in which the drive of the jaw members of the surgical instrument is controlled according to the rotation angle of the motor, the decrease in the gripping force of the jaw members can be suppressed.

A method of controlling a robotic surgical system according to a second aspect may be the method of controlling the robotic surgical system which includes: a surgical instrument including a pair of jaw members configured to be opened and closed by an elongate element; and a robotic arm which includes a motor configured to drive the elongate element and to which the surgical instrument is attached. The method may include: acquiring a second value corresponding to a rotation angle of the motor when a predetermined current value is reached; and performing calibration that changes, based on the acquired second value and a first value stored in advance that corresponding to the rotation angle of the motor when the predetermined current value is reached, a command angle for a tightening operation of the jaw members.

According to the second aspect, the method includes: acquiring the second value corresponding to the rotation angle of the motor when the predetermined current value is reached, the second value corresponding to the first value corresponding to the rotation angle of the motor when the predetermined current value is reached; and the step of performing calibration that changes, based on the acquired second value and the first value stored in advance, the command angle for the tightening operation of the jaw members. Accordingly, in a configuration in which the drive of the jaw members of the surgical instrument is controlled according to the rotation angle of the motor, it is possible to perform the calibration to compensate for the stretch of the elongate element. Therefore, it is possible to provide the method of controlling the robotic surgical system that is capable of suppressing the decrease in the gripping force of the jaw members in the configuration in which the drive of the jaw members of the surgical instrument is controlled according to the rotation angle of the motor.

Therefore, it is possible to provide a robotic surgical system and a method of controlling a robotic surgical system that are capable of suppressing a decrease in a gripping force of jaw members in a configuration in which a drive of the jaw members of a surgical instrument is controlled based on a rotation angle of a motor.

BRIEF DESCRIPTION OF DRAWINGS

FIG. 1 is a diagram illustrating a configuration of a robotic surgical system according to an embodiment.

FIG. 2 is a block diagram illustrating a view of a control-related configuration of the robotic surgical system according to an embodiment.

FIG. 3 is a diagram illustrating a view of a configuration of an operation handle according to an embodiment.

FIG. 4 is a diagram illustrating a perspective view of a state where a surgical instrument is attached via an adaptor to a robot arm according to an embodiment.

FIG. 5 is a diagram illustrating an exploded perspective view of a state where the surgical instrument is attached via the adaptor to the robot arm according to an embodiment.

FIG. 6 is a diagram illustrating a perspective view of the surgical instrument according to an embodiment as seen from below.

FIG. 7 is a diagram illustrating a perspective view of a state where a cover part is detached from a base body of the surgical instrument according to an embodiment.

FIG. 8 is a diagram illustrating a plan view of a state where the cover part is detached from the base body of the surgical instrument according to an embodiment.

FIG. 9 is a diagram illustrating a perspective view of an end effector of the surgical instrument according to an embodiment.

FIG. 10 is a diagram illustrating a pair of jaw members, a motor, a decelerator, a current detector, a position detector, and a controller according to an embodiment.

FIG. 11 is a graph for explaining calibration according to an embodiment.

FIG. 12 is a flowchart illustrating a control process when the surgical instrument is attached to the robot arm according to an embodiment.

FIG. 13 is a flowchart for explaining a control process in a calibration mode according to an embodiment.

FIG. 14 is a graph for explaining calibration according to a modified example.

FIG. 15 is a graph for explaining calibration according to a modification of the example illustrated in FIG. 14.

DETAILED DESCRIPTION

Descriptions are provided hereinbelow for embodiments based on the drawings. In the respective drawings referenced herein, the same constituents are designated by the same reference numerals and duplicate explanation concerning the same constituents is omitted. All of the drawings are provided to illustrate the respective examples only.

Descriptions are provided hereinbelow for an embodiment based on the drawings.

(Configuration of Robotic Surgical System)

A configuration of a robotic surgical system 100 according to an embodiment is described with reference to FIGS. 1 and 2.

As illustrated in FIG. 1, the robotic surgical system 100 includes a remote control apparatus 10 which is an operator-side device, and a patient-side apparatus 20 which is a surgery assist robot. The remote control apparatus 10 is provided to remotely control medical equipment provided to the patient-side apparatus 20. When an operator, as a surgeon, inputs an action mode instruction to be executed by the patient-side apparatus 20, to the remote control apparatus 10, the remote control apparatus 10 transmits the action mode instruction to the patient-side apparatus 20 through a controller 24. In response to the action mode instruction transmitted from the remote control apparatus 10, the patient-side apparatus 20 operates the medical equipment, including surgical instruments 40 attached to robot arms 21a and an endoscope 50 attached to a robot arm 21b. This allows minimally invasive surgery. Note that the controller 24 is an example of a controller or a control device.

The patient-side apparatus 20 constitutes an interface to perform a surgery for a patient P. The patient-side apparatus 20 is positioned beside an operation table 30 on which the patient P is laid. The patient-side apparatus 20 includes the plurality of robot arms 21a and 21 b, an arm base 22, a positioner 23, the controller 24, a storage 25, and a temporary storage 26. An endoscope 50 is attached to one robot arm 21b among the plural robot arms 21a and 21 b, and the surgical instruments 40 are attached to the other robot arms 21a. The robot arms 21a and 21 b are commonly supported by the arm base 22. Each of the plural robot arms 21a and 21b includes plural joints. Each joint includes a driver including a servo-motor and a position detector such as an encoder or the like. The robot arms 21a and 21 b are configured so that the medical equipment attached to each of the robot arms 21a and 21b is controlled by a driving signal given through the controller 24 and performs a desired movement.

The arm base 22 is supported by a positioner 23 placed on the floor of an operation room. The positioner 23 includes a vertical articulated robot. The positioner 23 is configured to move the position of the arm base 22 three-dimensionally. The controller 24 is a control circuit including an arithmetic unit such as a CPU and/or the like, and a memory such as a ROM, a RAM, and/or the like. The storage 25 is a data storage, and stores a threshold value $\theta_{S1}$ which will be described later and a threshold value $\theta_{S2}$ which will be described later. The temporary storage 26 stores a difference $\Delta\theta$, which will be described later. The storage 25 and the temporary storage 26 are provided in a robot body 27 on which the robot arms 21a and 21 b are provided. The temporary storage 26 is an example of a second storage. The threshold value $\theta_{S1}$ is an example of a second threshold value. The threshold value $\theta_{S2}$ is an example of a first threshold value.

The surgical instruments 40 as the medical equipment are detachably attached to the distal ends of the robot arms 21a. Each surgical instrument 40 includes: a housing 41 (see FIG. 4) which is to be attached to the robot arm 21a; an elongate shaft 42 (see FIG. 4); and an end effector 43 (see FIG. 4) which is provided at a tip portion (a distal end portion) of the shaft 42. The end effector 43 may be grasping forceps, scissors, a hook, a high-frequency knife, a snare wire, a clamp, a stapler, a clip applier, an electric knife, or a needle, for example. The end effector 43 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effectors 43 of the surgical instruments 40 are then located near a surgery site.

To the distal end of the robot arm 21b, the endoscope 50 as the medical equipment is detachably attached. The endoscope 50 captures an image in a body cavity of the patient P. The captured image is outputted to the remote control apparatus 10. The endoscope 50 may be a 3D endoscope capable of capturing a three-dimensional image or a 2D endoscope. In surgeries using the patient-side apparatus 20, the robot arm 21*b* introduces the endoscope 50 into the body of the patient P through a trocar placed on the body surface of the patient P. The endoscope 50 is then located near the surgery site.

The remote control apparatus 10 constitutes an interface with the operator. The remote control apparatus 10 is an apparatus that allows the operator to operate the medical equipment attached to the robot arms 21*a* and 21 *b*. Specifically, the remote control apparatus 10 is configured to transmit action mode instructions which are inputted by the operator and are to be executed by the surgical instruments 40 and the endoscope 50, to the patient-side apparatus 20 through the controller 24. The remote control apparatus 10 is installed beside the operation table 30 so that the operator can see the condition of the patient P very well while operating the remote control apparatus 10, for example. The remote control apparatus 10 may be configured to transmit the action mode instructions wirelessly and installed in a room different from the operation room where the operation table 30 is installed.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 43 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object. Further, the action modes may include an action to supply current to a bipolar or monopolar instrument to burn off the surgery site.

The action modes to be executed by the endoscope 50 include the position and posture of the distal end of the endoscope 50 and setting of the zoom magnification, for example.

As illustrated in FIGS. 1 and 2, the remote control apparatus 10 includes operation handles 11, an operation pedal section 12, a display 13, a touch panel 14, and a control apparatus 15.

The operation handles 11 are provided in order to remotely operate the medical equipment attached to the robot arms 21*a* and 21*b*. Specifically, the operation handles 11 accept operations by the operator for operating the medical equipment (the surgical instruments 40 and endoscope 50). The operation handles 11 are composed of two operation handles 11 arranged side by side in the horizontal direction. One of the two operation handles 11 is operated by the right hand of the operator while the other of the two operation handle 11 is operated by the left hand of the operator.

The operation handles 11 extend from the rear side of the remote control apparatus 10 toward the front side. The operation handles 11 are configured to move in a predetermined three-dimensional operation region. Specifically, the operation handles 11 are configured to be movable in a vertical direction, a horizontal direction, a front-rear direction, and a rotational direction.

As illustrated in FIG. 3, the operation handles 11 are hand controllers to be operated by the hands of the operator. The operation handle 11 includes a support member 11*a*, a pair of grip members 11*b* provided on both sides of the support member 11*a* with the support member 11*a* being interposed between the pair of grip members 11*b*, and a finger insertion portion 11*c* provided in each of the pair of grip members 11*b*. The operator inserts fingers (such as (thumb, middle finger, etc.) into the pair of finger insertion portions 11*c* to operate the operation handle 11. That is, a proximal end of each of the pair of grip members 11*b* is rotatably connected to a support member 11*a*. By increasing or decreasing an open angle between the pair of grip members 11*b* (a grip open angle), an open angle between a pair of jaw members 43*a* and 43*b*, which will be described later, is changed. A command for opening and closing the pair of jaw members 43*a* and 43*b* is input to the operation handle 11. The open angle between the pair of gripping members 11*b* is detected by a sensor, for example. For example, the operation handle 11 is provided with a hole sensor at the support member 11*a* and with a magnet at one or each of the pair of grip members 11*b*, so that the open angle between the pair of grip members 11*b* can be detected. Alternatively, the operation handle 11 is provided with a hole sensor at one of the pair of grip members 11*b* and with a magnet at the other of the pair of grip members 11*b*, so that the open angle between the pair of grip members 11*b* can be detected. Based on a signal relating to the detected open angle between the pair of grip members 11*b*, the pair of jaw members 43*a* and 43*b* are controlled to open and close.

As illustrated in FIG. 1, the remote control apparatus 10 and patient-side apparatus 20 constitute a master-slave system in terms of controlling movements of the robot arm 21*a* and the robot arms 21*b*. The operation handles 11 constitute a controlling part on the master side in the master-slave system, and the robot arms 21*a* and 21*b* holding the medical equipment constitute an acting part on the slave side. When the operator operates the operation handles 11, the movement of one of the robot arms 21*a* or 21 *b* is controlled so that the distal end portion (the end effector 43 of the surgical instrument 40) of the robot arm 21*a* or the distal end portion (the endoscope 50) of the robot arm 21*b* moves following the movement of the operation handles 11.

The patient-side apparatus 20 controls the movement of the robot arms 21*a* in accordance with the set motion scaling ratio. When the motion scaling ratio is set to ½, for example, the end effectors 43 of the surgical instruments 40 move ½ of the movement distance of the operation handles 11. This allows for precise fine surgery.

The operation pedal section 12 includes plural pedals to execute medical equipment-related functions. The plural pedals include a coagulation pedal, a cutting pedal, a camera pedal, and a clutch pedal. The plural pedals are operated by a foot of the operator.

The coagulation pedal enables the surgical instrument 40 to coagulate a surgery site. Specifically, when the coagulation pedal is operated, voltage for coagulation is applied to the surgical instrument 40 to coagulate the surgery site. The cutting pedal enables the surgical instrument 40 to cut the surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. That is, the position and orientation of the endoscope 50 are controllable by the operation handles 11 while the camera pedal is being pressed. The endoscope 50 is controlled by using both of the right and left operation handles 11, for example. Specifically, when the operator rotates the right and left operation handles 11 about the middle point between the right and left operation handles 11, the endoscope 50 is rotated. When the operator presses the right and left operation handles 11 together, the endoscope 50 goes forward into the body cavity. When the operator pulls the right and left operation handles 11 together, the endoscope 50 goes back. When the operator moves the right and left operation handles 11 together up, down, right, or left, the endoscope 50 moves up, down, right, or left, respectively.

The clutch pedal is used to temporarily disconnect operation-related connection between the robot arms 21a and the operation handles 11 to stop movement of the surgical instruments 40. Specifically, when the clutch pedal is being pressed, the robot arms 21a of the patient-side apparatus 20 do not work even if the operation handles 11 are operated. For example, when the operation handles 11 are operated and moved to the edge of the range of movement, the operator operates the clutch pedal to temporarily disconnect the operation-related connection and then returns the operation handles 11 to the center of the range of movement. When the operator stops operating the clutch pedal, the operation handles 11 are again connected to the robot arms 21a. The operator restarts the operation for the operation handles 11 around the center thereof.

The display 13 is configured to display images captured by the endoscope 50. The display 13 comprises a scope type display or a non-scope type display. (Note that FIG. 1 illustrates a scope type display.) The scope type display is a display configured in such a manner that the operator looks into the display. The non-scope type display is a display like an open-type display that includes a flat screen and the operator is able to see without looking into, such as normal displays for personal computers.

When the scope type display is attached, the scope type display displays 3D images captured by the endoscope 50 attached to the robot arm 21b of the patient-side apparatus 20. When the non-scope type display is attached, the non-scope type display also displays 3D images captured by the endoscope 50 provided for the patient-side apparatus 20. Here, when the non-scope type display is attached, 2D images captured by the endoscope 50 provided to the patient-side apparatus 20 may be displayed.

The touch panel 14 serves as an operation section and a display section. The touch panel 14 displays a screen for setting operations for the remote control apparatus 10 and receives setting operations for the remote control apparatus 10.

As illustrated in FIG. 2, the control apparatus 15 includes a controller 151, a storage 152, and an image controller 153, for example. The controller 151 includes an arithmetic unit such as a CPU. The storage 152 includes a memory, such as a ROM and a RAM. The control apparatus 15 may be composed of a single controller performing centralized control or may be composed of plural controllers that perform decentralized control in cooperation with each other. The controller 151 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 151 transmits the action mode instruction to the corresponding robot arm 21a through the controller 24. The robot arm 21a is thereby driven by the controller 24 and thus movement of the surgical instrument 40 attached to the robot arm 21a is controlled.

When determining that the action mode instruction inputted by the operation handles 11 is to be executed by the endoscope 50, the controller 151 transmits the action mode instruction to the robot arm 21b through the controller 24. The robot arm 21b is thereby driven for control of movement of the endoscope 50 attached to the robot arm 21b.

The storage 152 stores control programs corresponding to the types of the surgical instrument 40, for example. The controller 151 reads the stored control programs according to the types of the attached surgical instruments 40.

The action mode instructions from the operation handles 11 and/or the operation pedal section 12 of the remote control apparatus 10 thereby cause the respective surgical instruments 40 to perform proper movements.

The image controller 153 transmits images acquired by the endoscope 50 to the display 13. The image controller 153 performs processing and modifying the images when needed.

(Configurations of Surgical Instrument, Adaptor, Drape, and Robot Arm)

With reference to FIGS. 4 to 6, the configurations of the surgical instrument 40, an adaptor 60, a drape 70, and the robot arm 21a are described.

Here, the direction in which the surgical instrument 40 extends (the direction in which the shaft 42 extends) is defined as a Y direction, the distal side (the side toward the end effector 43) of the surgical instrument 40 along the Y direction is defined as a Y1 direction, and the opposite side of the Y1 direction is defined as a Y2 direction. The direction in which the surgical instrument 40 and the adaptor 60 are adjacent to each other is defined as a Z direction, the surgical instrument 40 side along the Z direction is defined as a Z1 direction, and the opposite side of the Z1 direction is defined as a Z2 direction. Further, the direction orthogonal to the Y direction and the Z direction is referred to as an X direction, one side along the X direction is referred as an X1 direction, and the other side along the X direction is referred to as an X2 direction.

As illustrated in FIGS. 4 and 5, the surgical instrument 40 is removably attached to the robot arm 21a. Specifically, the surgical instrument 40 is detachably attached to the robot arm 21a via the adaptor 60. The adaptor 60 is a drape adaptor configured to sandwich a sterile drape 70 to cover the robot arm 21a, in conjunction with the robot arm 21a.

The surgical instrument 40 is attached to the Z1 side of the adaptor 60. The adaptor 60 is attached to the Z1 side of the robot arm 21a.

The robot arm 21a is used in a clean area and is covered with the drape 70. In operation rooms, clean technique is used in order to prevent surgical incision sites and medical equipment from being contaminated by pathogen, foreign matters, or the like. The clean technique defines a clean area and a contaminated area, which is outside the clean area. The surgery sites are located in the clean area. Members of the surgical team, including the operator, make sure that only sterile objects are placed in the clean area during surgery and perform sterilization for an object which is to be moved to the clean area from the contaminated area. Similarly, when an assistant, as one of the members of the surgical team including the operator, places their hands in the contaminated area, the members sterilize their hands before directly touching objects located in the clean area. Instruments used in the clean area are sterilized or are covered with the drapes 70 that are sterilized.

As illustrated in FIG. 5, the drape 70 includes a body section 71 that covers the robot arm 21a and an attachment section 72 sandwiched between the robot arm 21a and the adaptor 60. The body section 71 is made of a flexible film member that is formed in a film-shape. The flexible film member is made of a resin material, such as thermoplastic polyurethane and polyethylene. The body section 71 includes an opening so that the robot arm 21a is engaged with the adaptor 60. To the opening of the body section 71, the attachment section 72 is provided. The attachment section 72 is made of a resin mold member. The resin mold member is made of a resin member such as polyethylene terephthalate. The attachment section 72 is harder (less flexible) than the body section 71. The attachment section 72 includes an opening so that the robot arm 21a is engaged with the adaptor 60. The opening of the attachment section 72 may be provided corresponding to the section where the robot arm 21a is engaged with the adaptor 60. The opening of the attachment section 72 may include plural openings corresponding to plural sections at which the robot arm 21a is engaged with the adaptor 60.

As illustrated in FIGS. 5 and 6, the surgical instrument 40 includes plural (four) driven members 44a, 44b, 44c, and 44d, and a storage 45. The storage 45 is provided in the housing 41. The storage 45 stores a serial number representing the surgical instrument 40, a number of times the surgical instrument 40 has been used, and values $\theta_1$ and $\theta_0$, which will be described later. in the embodiment, the value $\theta_1$ is set to approximately half the value $\theta_0$. When the surgical instrument 40 is attached to the robot arm 21a, the storage 45 is communicatively connected to the controller 24. Note that the storage 45 is an example of a first storage. The value $\theta_1$ is an example of a first value. The value $\theta_0$ is an example of a third value.

The driven members 44a to 44d are provided within the housing 41 and are rotatable about the respective rotation axes extending along the Z axis. The plural driven members 44a to 44d are provided to operate (drive) the end effector 43. The driven members 44b to 44d are connected to the end effector 43 via cables A, serving as elongate elements, passing through the inside of the shaft 42. With this, rotations of the driven members 44b to 44d drive the cables A, which operate (drive) the end effector 43. In addition, the driven member 44a is connected to the shaft 42 through gears 42a (see FIG. 7). With this, the shaft 42 is rotated with rotation of the driven member 44a, and the end effector 43 is also rotated with rotation of the shaft 42.

To transmit driving forces from the robot arm 21a to the end effector 43, each of the driven members 44a to 44d includes a projection 441 or 442, which is engaged with a corresponding one of drive transmission members 61 of the adaptor 60. Each of the projections 441 and 442 is projected from the Z2 side surface of the corresponding driven member 44a to 44d toward the side of the adaptor 60 (the Z2 side). Each of the projections 441 and 442 includes plural projection portions that arranged in a straight line. The protrusions 441 provided to the driven members 44a and 44b have different shapes from that of the protrusions 442 provided to the driven members 44c and 44d.

As illustrated in FIG. 5, the adaptor 60 includes a plurality (four) of the drive transmission members 61. The drive transmission members 61 are configured to transmit the driving forces from the robot arm 21a to the driven members 44a to 44d of the surgical instrument 40. That is, the drive transmission members 61 are provided so as to correspond to the driven members 44a to 44d of the surgical instrument 40. The drive transmission members 61 are rotatable about the respective rotation axes, which extend along the Z direction.

Each of the drive transmission members 61 includes an engagement recess 611 which is engaged with the projection 441 or 442 of the corresponding driven member 44a to 44d of the surgical instrument 40. The engagement recess 611 is located at the surgical instrument 40 side (the Z1 side) of the drive transmission member 61 and is recessed from the Z1 side surface of the drive transmission member 61, toward the Z2 direction, opposite to the surgical instrument 40. Each of the drive transmission members 61 includes an engagement recess, which is provided on the Z2 side surface thereof and is configured to be engaged with a corresponding engagement projection 213 of the robot arm 21a.

The robot arm 21a includes a frame 211, plural (four) drive parts 212, and plural engagement projections 213. The plural drive parts 212 are provided corresponding to the plural (four) driven members 44a to 44d of the surgical instrument 40 and corresponding to the plural (four) drive transmission members 61 of the adaptor 60. The drive part 212 is configured to drive the engagement projection 213 to rotate about a rotation axis thereof extending in the Z direction. The engagement projection 213 is engaged with the engagement recess provided on the Z2 side surface of the drive transmission member 61. The engagement projection 213 is projected from the Z1 side surface of the robot arm 21a toward the Z1 side (the adaptor 60 side). The drive parts 212 are configured to drive the drive transmission members 61 of the adaptor 60, engaged with the engagement projections 213, to rotate about the rotational axes extending in the Z direction, so as to drive the driven members 44a to 44d of the surgical instrument 40, engaged with the drive transmission members 61, to rotate about the rotational axes extending in the Z direction.

(Detailed Configuration of Surgical Instrument)

Next, with reference to FIGS. 7 to 9, the configuration of the surgical instrument 40 is described in detail below. Here, the case is described below in which the end effector 43 of the surgical instrument 40 is a grasping forceps including the pair of jaw members 43a and 43b. Note that the surgical instrument of the disclosure includes at least a pair of jaw members, and the pair of jaw members may be scissors or the like, for example.

As illustrated in FIGS. 7 and 8, the cables A are wound around the driven members 44b to 44d of the surgical instrument 40. That is, the cables A are connected to the driven members 44b to 44d.

The cable A3 is wound around the driven member 44b. Specifically, a first portion A3a of the cable A3 is wound in the clockwise direction around an upper portion of the driven member 44b, and a second portion A3b of the cable A3 is wound in the counterclockwise direction around a lower portion of the driven member 44b.

The cable A1 is wound around the driven member 44c of the surgical instrument 40. Specifically, a first portion A1a of the cable A1 is wound in the clockwise direction around an upper portion of the driven member 44c, and a second portion A1b of the cable A1 is wound in the counterclockwise direction around a lower portion of the driven member 44c.

The cable A2 is wound around the driven member 44d. Specifically, a first portion A2a of the cable A2 is wound in the clockwise direction around an upper portion of the driven member 44d, and a second portion A2b of the cable A1 is wound in the counterclockwise direction around a lower portion of the driven member 44d.

The cables A extend respectively from the driven members 44b to 44d through the shaft 42 to the end effector 43, are wound around the end effector 43, and return through the shaft 42 to the driven members 44b to 44d. In addition, the cables A are hung on pulleys 46. The pulleys 46 are retained by a pulley retainer 461.

As illustrated in FIGS. 8 and 9, when the driven member 44c rotates about the rotary axis thereof, the rotation of the driven member 44c operates the jaw member 43a, which is one of the jaw members 43a and 43b of the end effector 43. Specifically, the driven member 44c is rotated by the drive part 212 to drive the cable A1. The cable A1 extends through the inside of the shaft 42 and connects the jaw member 43a and the driven member 44c. Specifically, the cable A1 is wound around a pulley 43d provided at the base of the jaw member 43a. When the driven member 44c is rotated in the C1 direction (see FIG. 8), the first portion A1a of the cable A1 is pulled and the second portion A1b of the cable A1 is fed, so as to drive the jaw member 43a to move in the C1a direction (see FIG. 9), which is a direction to open the jaw member 43a. When the driven member 44c is rotated in the C2 direction opposite to the C1 direction (see FIG. 8), the first portion A1a of the cable A1 is fed and the second portion A1b of the cable A1 is pulled, so as to drive the jaw member 43a to move in the C2a direction (see FIG. 9), which is a direction to close the jaw member 43a.

When the driven member 44d rotates about the rotary axis thereof, the rotation of the driven member 44d operates the jaw member 43b, which is one of the jaw members 43a and 43b of the end effector 43. Specifically, the driven member 44d is rotated by the drive part 212 to drive the cable A2. The cable A2 extends through the inside of the shaft 42 and connects the jaw member 43b and the driven member 44d. Specifically, the cable A2 is wound around a pulley 43e provided at the base of the jaw member 43b. When the driven member 44d is rotated in the C3 direction (see FIG. 8), the first portion A2a of the cable A2 is pulled and the second portion A2b of the cable A2 is fed, so as to drive the jaw member 43b to move in the C3a direction (see FIG. 9), which is a direction to open the jaw member 43b. When the driven member 44d is rotated in the C4 direction opposite to the C3 direction (see FIG. 8), the first portion A2a of the cable A2 is fed and the second portion A2b of the cable A2 is pulled, so as to drive the jaw member 43b to move in the C4a direction (see FIG. 9), which is a direction to close the jaw member 43b. The jaw members 43a and 43b are opened and closed with respect to each other by the movements of the cables A of the driven members 44b and 44c. Note that the cables A1 and A2 are examples of elongate elements.

By being rotated about the rotation axis thereof, the driven member 44b operates a wrist portion 43c of the end effector 43. Specifically, the driven member 44b is rotated by the drive part 212 to drive the cable A3. The cable A3 extends through the inside of the shaft 42 and connects the wrist portion 43c and the driven member 44b. When the driven member 44b is rotated in the C5 direction (see FIG. 8), the first portion A3a of the cable A3 is pulled and the second portion A3b of the cable A3 is advanced, so as to drive the wrist portion 43c to move in the C5a direction (see FIG. 9). When the driven member 44b is rotated in the C6 direction opposite to the C5 direction (see FIG. 8), the second portion A3b of the cable A3 is pulled and the first portion A3a of the cable A3 is fed, so as to drive the wrist portion 43c to move in the C6a direction, which is opposite to the C5a direction (see FIG. 9).

When the drive part 212 rotates the driven member 44a about the rotation axis thereof with the gear portion 443 of the driven member 44a being engaged with a gear portion 42a connected to the proximal end of the shaft 42, the shaft 42 is driven to operate the end effector 43. Specifically, when the driven member 44a rotates in the C7 direction (see FIG. 8), the shaft 42 is driven to rotate in the C7a direction (see FIG. 9) and thus the end effector 43 is driven to rotate in the C7a. When the driven member 44a rotates in the C8 direction (see FIG. 8), the shaft 42 is driven to rotate in the C8a direction, which is opposite to the C7a direction (see FIG. 9), and thus the end effector 43 is driven to rotate in the C8a direction.

(Configuration Relating to Opening and Closing Jaw Members)

Next, a configuration relating to opening and closing of the jaw members 43a and 43b will be described with reference to FIGS. 10 and 11.

As illustrated in FIG. 10, each drive part 212 includes a motor 212a, a decelerator 212b, and a position detector 212c. The motor 212a is composed of a servo motor, and is a drive source that drives the cable A1 (A2) and the jaw member 43a (43b). The decelerator 212b reduces a rotation speed of the motor 212a and outputs the reduced rotation. The position detector 212c is composed of an absolute encoder and detects a rotation angle of the motor 212a. Further, a current detector 214 is provided for the motor 212a. The current detector 214 detects a current value of the motor 212a.

The controller 24 drives the motors 212a based on a signal from the operation handles 11. With this, the decelerator 212b, the engagement protrusion 213, the drive transmission member 61, and the driven members 44c, 44d are rotated, so as to drive the cables A1, A2. As a result, the jaw members 43a and 43b are opened and closed. The controller 24 drives the motor 212a such that the open angle between the jaw members 43a and 43b becomes an open angle that corresponds to a signal from the operation handles 11 (a target open angle). The controller 24 controls, based on the detection result of the rotation angle of the motor 212a detected by the position detector 212c, the rotation angle of the motor 212a such that the rotation angle corresponds to the target open angle. That is, the controller 24 controls the driving of the jaw members 43a and 43b by the rotation angle of the motor 212a.

For example, in the following cases, it is more effective to control the motor 212a that drives the jaw members 43a and 43b according to the rotation angle of the motor 212a rather than controlling the motor 212a that drives the jaw members 43a and 43b according to the torque. That is, in order to reduce the size of the robot arm 21a around the surgical field so as to ensure a working area, it is effective to reduce the size of the motor 212a. In order to reduce the size of the motor 212a, it is effective to use the decelerator 212b having a high reduction ratio. However, if the decelerator 212b having the high reduction ratio is used in a case in which the motor 212a is torque-controlled, the behavior of the distal end side of the surgical instrument 40 is less likely to be reflected as a change in the torque of the motor 212a. This makes it difficult to detect the behavior of the distal end side of the surgical instrument 40 by detecting the change in the torque of the motor 212a. In order to solve this problem, it is effective to control the rotation angle of the motor 212a that drives the jaw members 43a and 43b.

In addition, by further rotating the motor 212a in the closing direction of the jaw members 43a and 43b from a state in which the jaw members 43a and 43b are closed (i.e., a state in which the open angle is zero), a tightening force (gripping force) can be generated by the jaw members 43*a* and 43*b*. Hereinafter, a command angle by which the jaw members 43*a* and 43*b* are further closed from the state in which the open angle between the jaw members 43*a* and 43*b* is zero is referred to as a tightening angle. in the embodiment, the tightening angle is a negative value, but is not limited thereto. The tightening angle is an example of a value corresponding to the rotation angle of the motor 212*a*, and is calculated by the following formula (1).

$$\theta = 2 \times Rp \times Rm \times \theta m \qquad (1)$$

Here, θ, Rp, Rm and θm are as follows:
  θ: Tightening angle
  Rp: Reduction ratio between the driven members 44*c* and 44*d* and the pulleys 43*d* and 43*e* of the jaw members 43*a* and 43*b*
  Rm: Reduction ratio of the decelerator 212*b*
  θm: Rotation angle of the motor 212*a*

Here, the surgical instrument 40 is washed and sterilized after each surgery and is used multiple times. Therefore, as the surgical instrument 40 is used over time, lengths of the cables A1 and A2 that drive the jaw members 43*a* and 43*b* may become elongated. When the lengths of the cables A1, A2 become elongated, even if the motor 212*a* is controlled to a predetermined rotation angle, the jaw members 43*a* and 43*b* cannot be sufficiently tightened, and the gripping force of the jaw members 43*a* and 43*b* decreases.

Therefore, in the embodiment, as illustrated in FIG. 11, the controller 24 performs calibration to compensate for the elongation of the cables A1 and A2. Specifically, the storage 45 stores in advance a tightening angle θ₁ when the current value reaches a predetermined value I₁. The controller 24 acquires a tightening angle 62 when the current value reaches the predetermined current value I₁, and performs calibration to change the command angle for the tightening operation of the jaw members 43*a* and 43*b* based on the acquired value θ₂ and the value θ₁ stored in the storage 45. Specifically, the controller 24 corrects a maximum tightening angle θ₀ based on the tightening angle θ₁ and the tightening angle θ₂. The maximum tightening angle is the tightening angle an absolute value of which is the largest. With this, it possible to perform the calibration to compensate for the elongation of the cables A1 and A2 in a configuration in which the drive of jaw members 43*a* and 43*b* of surgical instrument 40 is controlled by the rotation angle of the motor 212*a*. Accordingly, the decrease in the gripping force of the jaw members 43*a* and 43*b* caused by the elongation of the cables A1 and A2 can be suppressed in the configuration in which the drive of the jaw members 43*a* and 43*b* of surgical instrument 40 is controlled by the rotation angle of the motor 212*a*. In the graph of FIG. 11, the right side is the negative side.

In the embodiment, the storage 45 stores the maximum tightening angle θ₀ in advance. The maximum tightening angle θ₀ is an example of a value corresponding to a maximum rotation angle of the motor 212*a* in the closing direction of the jaw members 43*a* and 43*b*. The controller 24 corrects the value θ₀ based on the values θ₂ and θ₁. With this, it possible to correct the maximum tightening angle θ₀ between the jaw members 43*a* and 43*b*, and therefore to increase the maximum rotation angle of the motor 212*a* which can rotate in the closing direction of the jaw members 43*a* and 43*b*. As a result, it is possible to reliably prevent the decrease in the gripping force of the jaw members 43*a* and 43*b* caused by the elongation of the cables A1 and A2.

Specifically, in the embodiment, the controller 24 corrects the value θ₀ by adding the difference Δθ between the value θ₂ and the value θ₁ to the value θ₀. This allows the value θ₀ to be corrected simply by adding the difference Δθ between the values θ₂ and θ₁ to the value θ₀, so that the calibration correction process can be performed by a simple process. The controller 24 performs the calibration that changes the value θ₀ of the command angle to a value θ₀+Ae.

More specifically, in the embodiment, the controller 24 corrects the value θ₀ so that the jaw members 43*a* and 43*b* can close up to the tightening angle of (θ₀+Δθ) obtained by adding the difference Δθ between the tightening angle values θ₂ and θ₁ to the tightening angle value θ₀. This enables the jaw members 43*a* and 43*b* to be closed up to a tightening angle obtained by adding the difference Δθ between the tightening angle values θ₂ and θ₁ to the tightening angle value θ₀ (i.e., the maximum tightening angle θ₀+A8 taking into account the elongation of the cables A1, A2). Therefore, it is possible to more reliably suppress a decrease in the gripping force of the jaw members 43*a* and 43*b* caused by the elongation of the cables A1, A2 over time.

Here, the principle of calibration for compensating for the elongation of the cables A1 and A2 in the embodiment will be described. The storage 45 stores in advance, as initial values, the tightening angle value θ₁ when the current value reaches the predetermined value I₁, and a maximum tightening angle θ₀. The values θ₁ and θ₀ are stored in advance in the storage 45 by an operator at the manufacturer before the surgical instrument 40 is shipped from the manufacturer. At the manufacturer, the values θ₁ and θ₀ are obtained taking into account the initial slack of the cables A1 and A2. The value θ₀ is set to a value that enables the jaw members 43*a* and 43*b* to exert a predetermined gripping force. The absolute value of the value θ₀ is greater than the absolute value of the value θ₁.

The controller 24 starts the calibration from a state in which the jaw members 43*a* and 43*b* are closed (a state in which the open angle between the jaw members 43*a* and 43*b* is zero). The controller 24 drives the motor 212*a* to rotate to make the tightening angle the maximum tightening angle θ₀. In addition, in the course of rotating the motor 212*a* to close the jaw members 43*a* and 43*b* to a point where the value corresponding to the rotation angle of the motor 212*a* becomes the value θ₀ (as the target value), the controller 24 acquires the value θ₂. As the jaw members 43*a* and 43*b* are further closed from the state the jaw members 43*a* and 43*b* are closed, the current value of the motor 212*a* increases. The current value of the motor 212*a* is detected (monitored) by the current detector 214. in the case in which the cables A1, A2 are stretched, even when the tightening angle of the jaw members 43*a* and 43*b* reaches the value θ₁, the current value of the motor 212*a* reaches a value smaller than the predetermined current value I₁. The controller 24 obtains the tightening angle value θ₂ when the current value of the motor 212*a* reaches the predetermined current value I₁ based on the detection result of the current detector 214. In addition, the controller 24 calculates the difference Δθ between the value θ₂ and the value θ₁. The difference Δθ between the value θ₂ and the value θ₁ corresponds to the elongation of the cables A1 and A2 due to use. Further, the controller 24 corrects the value θ₀ so that the jaw members 43*a* and 43*b* are able to be closed up to a tightening angle θ₀+A8 obtained by adding the difference Δθ between the values θ₂ and θ₁ to the initial maximum tightening angle value θ₀. This can make the current response of the motor 212*a* in the state in which the cables A1 and A2 are elongated equivalent to the initial current response of the motor $212a$, thereby suppressing a decrease in the gripping force of the jaw members $43a$ and $43b$ caused by the elongation of the cables A1 and A2. Note that the absolute value of the value $\theta_0$ is greater than the absolute value of the value $\theta_2$.

Further, in the embodiment, the controller 24 determines, based on the threshold value $\theta_{S1}$, whether or not the value $\theta_2$ is within a predetermined range with respect to the value $\theta_1$. when it is determined that the value $\theta_2$ is within the predetermined range with respect to the value $\theta_1$, the controller 24 does not correct the value $\theta_0$. To the contrary, when it is determined that the value $\theta_2$ is out of the predetermined range with respect to the value $\theta_1$, the controller 24 corrects the value $\theta_0$. This makes it possible to avoid unnecessarily correcting the value $\theta_0$ when it is determined that the value $\theta_2$ is within the predetermined range relative to the value $\theta_1$ (that is, when the elongation of the cables A1 and A2 is small and thus the correction is not necessary). Further, when it is determined that the value $\theta_2$ is out of the predetermined range relative to the value $\theta_1$ (that is, when the extension of the cables A1 and A2 is large and thus the correction is necessary), the value $\theta_0$ is appropriately corrected.

Specifically, the controller 24 determines whether the value $\theta_2$ is within the range $\theta_1 \pm \theta_{S1}$. The threshold value $\theta_{S1}$ is not particularly limited, and may be a value obtained by converting a value (such as Y Newtons) that determines the upper and lower limits of the range (such as X±Y Newtons) of the set gripping force of the jaw members $43a$ and $43b$ into a tightening angle using a conversion coefficient. Note that when the range of the set gripping force differs depending on the type of the jaw members $43a$ and $43b$ (i.e., the type of the end effector 43), the threshold value $\theta_{S1}$ may be different for each type of the end effector 43. The threshold value $\theta_{S1}$ is a positive value in the embodiment, and is stored in the storage 25 provided in the robot body 27.

Further, in the embodiment, the controller 24 determines whether the difference $\Delta\theta$ between the value $\theta_2$ and the value $\theta_1$ is within the normal range based on the threshold value $\theta_{S2}$. When it is determined that the difference $\Delta\theta$ between the value $\theta_2$ and the value $\theta_1$ is within the normal range, the controller 24 corrects the value $\theta_0$. To the contrary, when it is determined that the difference $\Delta\theta$ between the value $\theta_2$ and the value $\theta_1$ is outside the normal range, the controller 24 reacquires the value $\theta_2$. As a result, when it is determined that the difference $\Delta\theta$ between the value $\theta_2$ and the value $\theta_1$ is within the normal range, the value $\theta_0$ is corrected so that the calibration can be performed appropriately. Further, when it is determined that the difference $\Delta\theta$ between the value $\theta_2$ and the value $\theta_1$ is outside the normal range, the value $\theta_2$ is acquired again, thereby making it possible to avoid acquiring an excessively large value $\theta_2$ (and difference $\Delta\theta$). As a result, it is possible to prevent the value $\theta_0$ from being corrected to an excessively large value based on an excessively large $\theta_2$ (and the difference $\Delta\theta$). With this, it possible to prevent the cables A1 and A2 from being damaged due to an excessive load being applied to the cables A1 and A2 caused by the value $\theta_0$ being corrected to an excessively large value.

Specifically, the controller 24 determines whether the difference $\Delta\theta$ between the value $\theta_2$ and the value $\theta_1$ is within the range of $\theta_{32} < \Delta\theta < 0$. The threshold value $\theta_{S2}$ is not particularly limited, and may be a common value regardless of the type of the end effector 43. In the embodiment, the threshold value $\theta_{S2}$ is a negative value and is obtained in advance by experiment or the like and stored in the storage 25 provided in the robot body 27.

In the embodiment, the storage 45 that stores the value $\theta_1$ is provided in the surgical instrument 40. This allows a different value $\theta_1$ for each surgical instrument 40 to be stored in advance in the storage 45 provided in the surgical instrument 40, so that an appropriate value $\theta_1$ for each surgical instrument 40 can be easily used when using the surgical instrument 40. In the embodiment, the storage 45 also stores the value $\theta_0$. As in the value $\theta_1$, this allows a different value $\theta_0$ for each surgical instrument 40 to be stored in advance in the storage 45 provided in the surgical instrument 40, so that an appropriate value $\theta_0$ for each surgical instrument 40 can be easily used when using the surgical instrument 40.

Further, in the embodiment, the temporary storage 26 that stores a correction value ($\Delta\theta$) based on the value $\theta_1$ and the value $\theta_2$ is provided in the robot body 27. As a result, even when the surgical instrument 40 is removed from the robot arm $21a$ during surgery and then reattached to the robot arm $21a$, there is no need to re-acquire the correction value ($\Delta\theta$) since the correction value ($\Delta\theta$) is stored in the temporary storage 26 provided in the robot body 27. As a result, it is possible to eliminate the need to re-acquire the correction value ($\Delta\theta$) each time the surgical instrument 40 is attached to the robot arm $21a$. The correction value ($\Delta\theta$) stored in the temporary storage 26 is reset (deleted) for each surgery (for example, each time the power to the robot body 27 is turned off or restarted). Therefore, it is possible to obtain an appropriate value $\Delta\theta$ for each surgery.

Further, in the embodiment, the controller 24 starts the calibration at least one of the following times: when the surgical instrument 40 is attached to the robot arm $21a$; and when a user interface (such as the operation handle 11 or the touch panel 14) that accepts an operation to execute the calibration is operated. As a result, in the case in which the calibration is started at the time when the surgical instrument 40 is attached to the robot arm $21a$, the calibration is executed simply by attaching the surgical instrument 40 to the robot arm $21a$, thereby saving the user effort. In the case in which the calibration is started at the timing when the user interface that accepts the operation to execute the calibration is operated, the calibration is executed at a timing desired by the user. The operation handle 11 or the touch panel 14 is an example of a user interface.

Further, in the case where the calibration is started at the timing when the surgical instrument 40 is attached to the robot arm $21a$, the controller 24 determines whether or not the surgical instrument 40 is attached to the robot arm $21a$ for the first time during the surgery. When it is determined that the attachment of the surgical instrument 40 to the robot arm $21a$ is for the first time during the surgery, the controller 24 starts the calibration, and when it is determined that the attachment of the surgical instrument 40 to the robot arm $21a$ is not for the first time during the surgery, the controller 24 does not start the calibration. This allows the calibration to be started appropriately when it is determined that the surgical instrument 40 is attached to the robot arm $21a$ for the first time during the surgery (i.e., when the calibration has not been performed). Further, when it is determined that the attachment of the surgical instrument 40 to the robot arm $21a$ is not the first time during the surgery (i.e., when the calibration has already been performed), the calibration is not started, thereby preventing unnecessary calibration from being performed.

When the surgical instrument 40 is attached to the robot arm $21a$, the controller 24 obtains the serial number of the surgical instrument 40 from the storage 45, and determines based on the obtained serial number of the surgical instrument 40 whether or not this is the first time that the surgical instrument 40 has been attached to the robot arm 21*a* during the surgery. Specifically, when the obtained serial number of the surgical instrument 40 is not stored in the storage 25 or the temporary storage 26, the controller 24 determines that this is the first time that the surgical instrument 40 has been attached to the robot arm 21*a* during the surgery. In addition, the controller 24 stores the obtained serial number of the surgical instrument 40 in the storage 25 or the temporary storage 26. When the obtained serial number of the surgical instrument 40 is stored in the storage 25 or the temporary storage 26, the controller 24 determines that this is not the first time that the surgical instrument 40 has been attached to the robot arm 21*a* during the surgery (that is, this is the second or subsequent time). When the controller 24 determines that it is not the first time that the surgical instrument 40 is attached to the robot arm 21*a* during the surgery, the controller 24 does not start calibration and corrects $\theta_0$ using the correction value ($\Delta\theta$) at the time of the initial attachment.

Further, in the embodiment, the controller 24 corrects the value $\theta_0$ based on the value $\theta_2$, the value $\theta_1$, and the value $\theta_a$ corresponding to the rotation angle of the motor 212*a* that is determined in advance according to the number of times the surgical instrument 40 is used. This allows the value $\theta_0$ to be corrected not only based on the values $\theta_2$ and $\theta_1$ but also on the tightening angle $\theta_a$ that is determined in advance according to the number of times the surgical instrument 40 is used, thereby more reliably suppressing the decrease in the gripping force of the jaw members 43*a* and 43*b* caused by the elongation of the cables A1 and A2. The value $\theta_a$ is a fixed value determined according to the number of times the surgical instrument 40 is used, and is obtained in advance by experiment or the like. The value $\theta_a$ is an example of a fourth value.

(Control Process when Attaching Surgical Instrument)

Next, with reference to FIG. 12, a control process performed when the surgical instrument 40 is attached to the robot arm 21*a* will be described based on a flowchart. Note that here, the case will be described in which the calibration is started at the time when the surgical instrument 40 is attached to the robot arm 21*a*.

As illustrated in FIG. 12, first, in step S101, the surgical instrument 40 is attached to the robot arm 21*a* via the adapter 60. Then, in step S102, a matting operation mode is started. In the mating operation mode, the engagement projections 213 of the robot arm 21*a* are mated with the engagement recesses of the drive transmission members 61 of the adapter 60, and the engagement recesses 611 of the drive transmission members 61 of the adapter 60 are mated with the projections 441 and 442 of the driven members 44*a* to 44*d*.

Then, in step S103, it is determined whether or not the surgical instrument 40 is attached to the robot arm 21*a* for the first time during surgery. When it is determined that the attachment of the surgical instrument 40 to the robot arm 21*a* is the first time during the surgery, the process proceeds to step S104. Then, in step S104, a calibration mode in which calibration is performed is started. When the process of step S104 is completed, the process proceeds to step S106. The calibration mode process will be described in detail later.

To the contrary, when it is determined in step S103 that the attachment of the surgical instrument 40 to the robot arm 21*a* is not the first time during the surgery, the process proceeds to step S105. Then, in step S105, a correction of the tightening angle is executed. That is, in step S105, in the calibration mode at the first time attachment, which will be described later, the tightening angle is corrected in accordance with the formula: $\theta_{0c}=\theta_0+\theta_a+\Delta\theta$ (where $\theta_{0c}$ is the maximum tightening angle after correction). Then, the process proceeds to step S106.

In step S106, a gripping force check mode is started. In the gripping force check mode, it is determined whether or not the predetermined gripping force can be output as the gripping force by the jaw members 43*a* and 43*b*. Then, when it is determined that the predetermined gripping force can be output as the gripping force by the jaw members 43*a* and 43*b*, the control process is terminated.

(Control Process of Calibration Mode)

Next, a control process of the calibration mode will be described with reference to a flowchart illustrated in FIG. 13

As illustrated in FIG. 13, in step S201, a tightening operation of the jaw members 43*a* and 43*b* is performed. In the tightening operation, the jaw members 43*a* and 43*b* are driven to close to the tightening angle of $\theta_0+\theta_a+\Delta\theta$ (where $\Delta\theta=0$).

Then, in step S202, the rotation angle of the motor 212*a* when the current value reaches the predetermined value $I_1$ is obtained. At this time, the current value of the motor 212*a* is obtained taking into consideration the friction and inertia of the motor 212*a*. Further, the rotation angle of the motor 212*a* that is detected by the position detector 212*c* when the current value reaches the predetermined value $I_1$ is converted into the tightening angle of the jaw members 43*a* and 43*b* by the above described formula (1), thereby obtaining the tightening angle value $\theta_2$.

Then, in step S203 for the first time, it is determined, based on the threshold value $\theta_{S1}$, whether or not the value $\theta_2$ is within the predetermined range with respect to the value $\theta_1$. Specifically, it is determined whether the value $\theta_2$ is within the range of $\theta_1-\theta_{S1}\leq\theta_2-\Delta\theta\leq\theta_1+\theta_{S1}$ (where $\Delta\theta=0$). When it is determined that the value $\theta_2$ is within the predetermined range with respect to the value $\theta_1$, it means that it is determined that the elongation of the cables A1 and A2 is small and no correction is necessary, so that no correction is performed and the control process is terminated. In this case, $\theta_0$ stored in advance in the storage 45 is used as the maximum tightening angle.

Further, when it is determined in step S203 for the first time that the value $\theta_2$ is not within the predetermined range with respect to the value $\theta_1$, it means that it is determined that the elongation of the cables A1 and A2 is large and the correction is necessary, and the process proceeds to step S204.

Then, in step S204, the difference $\Delta\theta$ between the value $\theta_2$ and the value $\theta_1$ is obtained as the correction value.

Then, in step S205, it is determined based on the threshold value $\theta_{S2}$ whether or not the difference $\Delta\theta$ is within the normal range. Specifically, it is determined whether the difference $\Delta\theta$ is within the range of $\theta_{S2}<\Delta\theta<0$. When it is determined that the difference $\Delta\theta$ is within the normal range, the process proceeds to step S207.

Then, in step S207, the tightening angle correction is performed to correct the value $\theta_0$ based on the values $\theta_1$ and $\theta_2$. Specifically, the value $\theta_0$ is corrected by adding the difference $\Delta\theta$ between the value $\theta_1$ and the value $\theta_2$ to the value $\theta_0$. More specifically, the maximum tightening angle is corrected as expressed by the formula: $\theta_{0c}=\theta_0+\theta_a+\Delta\theta$ (where $\theta_{0c}$ is the corrected maximum tightening angle).

Then, in step S208, a re-tightening operation is performed that closes the jaw members 43*a* and 43*b* again. In the re-tightening operation, the jaw members 43*a* and 43*b* are driven to close up to the corrected maximum tightening angle $\theta_0c$. Then, the process proceeds to step S202. Then, in step S202, the tightening angle $\theta_2$ at which the current value becomes the predetermined value $I_1$ is obtained again.

Then, in step S203 for the second time after step S208, it is determined whether $\theta_2 - \Delta\theta$ (where $\Delta\theta = \theta_2 - \theta_1$) is within the range of $\theta_1 - \theta_{S1} \le \theta_2 - \Delta\theta \le \theta_1 + \theta_{S1}$. Here, $(\theta_2 - \Delta\theta)$ is $(\theta_2 - \theta_2 + \theta_1)$, which is $\theta_1$. Therefore, in step S203, it is determined that $\theta_2 - \Delta\theta$ is within the range of $\theta_1 - \theta_{S1} \le \theta_2 - \Delta\theta \le \theta_1 + \theta_{S1}$, and the control process is terminated with the correction being performed.

When it is determined in step S205 that the difference $\Delta\theta$ is not within the normal range, the process proceeds to step S209.

Then, in step S209, it is determined whether the difference $\Delta\theta$ is determined to be outside the normal range for two consecutive times. When it is not determined that the difference $\Delta\theta$ is determined to be outside the normal range for two consecutive times, the process proceeds to step S201. Then, the processes of step S201 to step S205 are repeated. To the contrary, when it is determined that the difference $\Delta\theta$ is determined to be outside the normal range for two consecutive times, the process proceeds to step S210. Then, in step S210, an error message is displayed and the control process is terminated.

(Modifications)

It should be understood that one or more embodiments described above are illustrated by way of example in every respect and do not limit the disclosure. The scope of the invention is indicated by claims, not by the explanation of the one or more embodiments described above, and includes equivalents to the claims and all alterations (modifications) within the same.

For example, in the embodiment described above, the case has been described in which the values corresponding to the rotation angles of the motor ($\theta_1$, $\theta_2$, $\theta_0$, etc.) are values that represent the tightening angles between the jaw members, but the invention is not limited to this. In the invention, the value corresponding to the rotation angle of the motor may represent a value other than the tightening angle between the jaw members. For example, the value corresponding to the rotation angle of the motor may be the rotation angle of the motor.

Further, in the embodiment described above, the case has been described in which the third value ($\theta_0$) is a value that corresponds to the maximum rotation angle of the motor in the closing direction of the jaw members, but the invention is not limited to this. In the invention, the third value may be a value having an absolute value greater than the value $\theta_1$ and corresponding to a rotation angle other than the maximum rotation angle of the motor in the closing direction of the jaw members.

In the embodiment described above, the case has been described in which it is determined whether or not the difference ($\Delta\theta$) between the second value ($\theta_2$) and the first value ($\theta_1$) is within the normal range, but the invention is not limited to this. In the invention, it is not necessary to determine whether the difference between the second value and the first value is within the normal range.

In the embodiment described above, the case has been described in which it is determined whether the second value ($\theta_2$) is within the predetermined range with respective to the first value ($\theta_1$), but the invention is not limited to this. In the invention, it is not necessary to determine whether the second value is within the predetermined range with respective to the first value.

In the embodiment described above, the case has been described in which the first storage (45) that stores the first value ($\theta_1$) and the third value ($\theta_0$) is provided in the surgical instrument, and the second storage (26) that stores the correction value ($\Delta\theta$) based on the first value and the second value ($\theta_2$) is provided in the robot body, but the invention is not limited to this. In the invention, the first storage may be provided in the robot body, and the second storage may be provided in the surgical instrument. Further, the second storage does not have to be a temporary storage.

In the embodiment described above, the case has been described in which it is determined whether or not the attachment of the surgical instrument to the robot arm is the first time during the surgery, but the invention is not limited to this. In the invention, the calibration may be started every time the surgical instrument is attached to the robot arm.

Further, in the embodiment described above, the case has been described in which the third value ($\theta_0$) is corrected based on the second value ($\theta_2$), the first value ($\theta_1$), and the fourth value ($\theta_a$), but the invention is not limited to this. In the invention, the fourth value ($\theta_a$) may not be used to correct the third value ($\theta_0$).

Further, in the embodiment described above, the case has been described in which the decrease in the gripping force of the jaw members caused by the elongation of the cables is suppressed in the configuration in which the drive of the jaw members of the surgical instrument is controlled according to the rotation angle of the motor. However, the invention is not limited to this. In the invention, a rod may be used as an elongate element, and a gear, a pulley, or a bearing may be used as a driven member, and the decrease in the gripping force of the jaw members caused by wear, seizure, galling, chipping, rust, etc., of the gear, pulley, bearing, and rod of the surgical instrument may be corrected.

Further, in the invention, the decrease in the gripping force due to wear of the jaw members may be corrected.

The functions of each of the elements disclosed herein may be carried out by a circuitry or a processing circuitry including a general purpose processor, a dedicated processor, an integrated circuit, an ASIC (application specific integrated circuit), a conventional circuit, or a combination of two or more of them, that is configured or programmed to perform the functions. A processor is considered as a processing circuitry or a circuitry because it contains transistors and other circuit elements. In the disclosure, a circuit, a unit, or a means may be either a hardware that is configured to perform the recited function(s) or a hardware that is programmed to perform the recited function(s). The hardware may be the hardware disclosed herein, or may be other known hardware that is programmed or configured to perform the recited function(s). If the hardware is a processor which is considered as a type of a circuit, a circuit, a means, or a unit is a combination of hardware and software, and the software is used to configure the hardware and/or the processor.

Further, in the embodiment described above, the case has been described in which the third value ($\theta_0$) as the command angle is corrected based on the second value ($\theta_2$) and the first value ($\theta_1$). However, a modified example illustrated in FIG. 14 may be used. In the modified example illustrated in FIG. 14, the controller 24 performs the calibration based on the value $\theta_2$ and a difference $\Delta\theta_2$ between the values $\theta_1$ and $\theta_0$, to change the command angle for closing the jaw members 43a and 43b without correcting the value $\theta_0$. In a modified example illustrated in FIG. 14, the value $\theta_1$ and the difference $\Delta\theta_2$ between the value $\theta_1$ and the value $\theta_0$ are stored in advance in the storage 45. During the calibration, the controller 24 acquires the value $\theta_2$ in the course of rotating the motor 212a to close the jaw members 43a and 43b so that the value corresponding to the rotation angle of the motor 212a becomes the value $\theta_1+\Delta\theta_2$ (the value $\theta_1+\Delta\theta_2$ as the target value). The controller 24 adds the difference $\Delta\theta_2$ to the value $\theta_2$. As a result, the controller 24 performs the calibration to change the command angle value $\theta_1+\Delta\theta_2$ to a value $\theta_2+\Delta\theta_2$. This allows the jaw members 43a and 43b to close up to the tightening angle equal to the sum of the value $\theta_2$ and the difference $\Delta\theta_2$.

FIG. 15 illustrates another modified example using the difference $\Delta\theta_2$. In this example, the value $\theta_0$ and the difference $\Delta\theta_2$ between the values $\theta_1$ and $\theta_0$ are stored in advance in the storage 45. In the calibration, the controller 24 acquires the value $\theta_2$ in the course of rotating the motor 212a to close the jaw members 43a and 43b to the point where the value corresponding to the rotation angle of the motor 212a becomes the value $\theta_0$ (the value $\theta_0$ is the target value). The controller 24 adds the difference $\Delta\theta_2$ to the value $\theta_2$. As a result, the controller 24 performs the calibration that changes the command angle value $\theta_0$ to the value $\theta_2+\Delta\theta_2$.

The invention claimed is:

1. A robotic surgical system, comprising:
a surgical instrument including a pair of jaw members configured to be opened and closed by an elongate element;
a robotic arm which includes a motor configured to drive the elongate element and to which the surgical instrument is attached;
a first storage that stores in advance a first value corresponding to a rotation angle of the motor when a predetermined current value is reached; and
a controller that is configured to acquire a second value corresponding to the rotation angle of the motor when the predetermined current value is reached, and perform calibration to change, based on the acquired second value and the first value stored in the first storage, a command angle for a tightening operation of the jaw members.

2. The robotic surgical system according to claim 1, wherein
the controller is configured to correct, based on the second value and the first value, a third value corresponding to the rotation angle of the motor in a closing direction of the jaw members.

3. The robotic surgical system according to claim 2, wherein
the first storage stores the third value corresponding to a maximum rotation angle of the motor in the closing direction of the jaw members, and
the controller is configured to correct the third value based on the second value and the first value, wherein the third value is the command angle.

4. The robotic surgical system according to claim 3, wherein
the controller is configured to correct the third value by adding a difference between the second value and the first value to the third value.

5. The robotic surgical system according to claim 2, wherein
the first value, the second value, and the third value are values representing the tightening angle of the jaw members.

6. The robotic surgical system according to claim 5, wherein
the third value is a value representing a maximum tightening angle of the jaw members corresponding to a maximum rotation angle of the motor in the closing direction of the jaw members, and the controller is configured to correct the third value so that the jaw members is able to be closed up to the tightening angle that is obtained by adding the tightening angle of a difference between the second value and the first value to the tightening angle of the third value.

7. The robotic surgical system according to claim 2, wherein
the controller is configured to determine whether or not the difference between the second value and the first value is within a normal range based on a first threshold value, correct the third value when it is determined that the difference between the second value and the first value is within the normal range, and re-acquire the second value when it is determined that the difference between the second value and the first value is outside the normal range.

8. The robotic surgical system according to claim 2, wherein
the controller is configured to determine based on a second threshold value whether the second value is within a predetermined range with respect to the first value, configured not to correct the third value when the second value is determined to be within the predetermined range with respect to the first value, and configured to correct the third value when the second value is determined to be outside the predetermined range with respect to the first value.

9. The robotic surgical system according to claim 1, wherein
the first storage is provided in the surgical instrument.

10. The robotic surgical system according to any one of claim 1, further comprising:
a robot body to which the robot arm is provided; and
a second storage that stores a correction value that is based on the second value and the first value, wherein the second storage is provided to the robot body.

11. The robotic surgical system according to claim 1, wherein
the controller is configured to start the calibration at least one of the following timings: when the surgical instrument is attached to the robot arm; and
when a user interface that accepts an operation to perform the calibration is operated.

12. The robotic surgical system according to claim 11, wherein
the controller is configured to determine whether or not an attachment of the surgical instrument to the robot arm is the first time during surgery, and configured to start the calibration when it is determined that the attachment of the surgical instrument to the robot arm is the first time during the surgery, and not to start the calibration when it is determined that the attachment of the surgical instrument to the robot arm is not the first time during the surgery.

13. The robotic surgical system according to claim 2, wherein
the controller is configured to correct the third value, based on the second value, the first value, and a fourth value corresponding to the rotation angle of the motor that is determined in advance according to a number of times the surgical instrument has been used.

14. The robotic surgical system according to claim 1, wherein
the elongate element is a cable.

15. The robotic surgical system according to claim 2, wherein an absolute value of the third value is greater than an absolute value of the first value.

16. The robotic surgical system according to claim 1, wherein the controller is configured to start the calibration from a state in which the jaw members are closed.

17. The robotic surgical system according to claim 2, wherein the controller is configured to acquire the second value in a course of rotating the motor to close the jaw members such that the value corresponding to the rotation angle of the motor becomes the third value.

18. A robotic surgical system, comprising:

a surgical instrument including a pair of jaw members configured to be opened and closed by an elongate element;

a robotic arm which includes a motor configured to drive the elongate element and to which the surgical instrument is attached;

a first storage that stores in advance a first value corresponding to a rotation angle of the motor when a predetermined current value is reached; and a controller that is configured to acquire a second value corresponding to the rotation angle of the motor when the predetermined current value is reached, and perform calibration to change, based on the acquired second value and the first value stored in the first storage, a command angle for a tightening operation of the jaw members.

19. The robotic surgical system according to claim 18, further comprising:

a robot body including the robot arm and a second storage that stores a correction value that is based on the second value and the first value.

20. A method of controlling a robotic surgical system comprising: a surgical instrument including a pair of jaw members configured to be opened and closed by an elongate element; and a robotic arm which includes a motor configured to drive the elongate element and to which the surgical instrument is attached, the method comprising:

acquiring a second value corresponding to a rotation angle of the motor when a predetermined current value is reached; and performing calibration that changes, based on the acquired second value and a first value stored in advance corresponding to the rotation angle of the motor for the predetermined current value, a command angle for a tightening operation of the jaw members.

* * * * *